(12) United States Patent
Suzuma et al.

(10) Patent No.: US 11,965,856 B2
(45) Date of Patent: Apr. 23, 2024

(54) METHOD AND DEVICE FOR DETECTING METAL RESIDUE IN ELECTRIC-RESISTANCE-WELDED STEEL PIPE

(71) Applicant: NIPPON STEEL CORPORATION, Tokyo (JP)

(72) Inventors: Toshiyuki Suzuma, Tokyo (JP); Yoshiyuki Nakao, Tokyo (JP)

(73) Assignee: NIPPON STEEL CORPORATION, Tokyo (JP)

( * ) Notice: Subject to any disclaimer, the term of this patent is extended or adjusted under 35 U.S.C. 154(b) by 802 days.

(21) Appl. No.: 16/971,223

(22) PCT Filed: Sep. 27, 2018

(86) PCT No.: PCT/JP2018/035869
§ 371 (c)(1),
(2) Date: Aug. 19, 2020

(87) PCT Pub. No.: WO2019/178233
PCT Pub. Date: Oct. 3, 2019

(65) Prior Publication Data
US 2021/0116417 A1  Apr. 22, 2021

(30) Foreign Application Priority Data

Mar. 27, 2018 (JP) .................................. 2018-060523

(51) Int. Cl.
*G01N 27/82* (2006.01)
*B23K 31/12* (2006.01)
(Continued)

(52) U.S. Cl.
CPC .......... *G01N 27/82* (2013.01); *B23K 31/125* (2013.01); *G01N 33/207* (2019.01); *B23K 2101/04* (2018.08)

(58) Field of Classification Search
CPC ..... G01N 27/85; G01N 33/207; B23K 31/125
See application file for complete search history.

(56) References Cited

U.S. PATENT DOCUMENTS 4,303,883 A * 12/1981 Mori .................. G01N 29/2412
324/243
4,481,824 A * 11/1984 Fujimoto ............... G01N 29/38
73/622
(Continued)

FOREIGN PATENT DOCUMENTS

CN      107710024 A    2/2018
JP      4-215046 A     8/1992
(Continued)

*Primary Examiner* — Dominic E Hawkins
(74) *Attorney, Agent, or Firm* — Birch, Stewart, Kolasch & Birch, LLP

(57) ABSTRACT

A method for detecting a metal residue present in an electric-resistance-welded steel pipe includes a first step of inserting the electric-resistance-welded steel pipe into an exciting coil while relatively moving the electric-resistance-welded steel pipe in a longitudinal direction and magnetizing the electric-resistance-welded steel pipe using a direct current at a field intensity capable of magnetizing the electric-resistance-welded steel pipe and the metal residue up to a magnetic saturation state by the exciting coil and a second step of inserting the electric-resistance-welded steel pipe into a detecting coil while relatively moving the electric-resistance-welded steel pipe in the longitudinal direction, detecting an induced electromotive force generated in the detecting coil by a change in a magnetic flux caused by the direct-current magnetization by the exciting coil in the first step as an output signal of the detecting coil, and detecting the metal residue present in the electric-resistance-welded steel pipe on the basis of the output signal of the detecting coil.

22 Claims, 8 Drawing Sheets

(51) Int. Cl.
 *G01N 33/207* (2019.01)
 *B23K 101/04* (2006.01)

(56) References Cited

U.S. PATENT DOCUMENTS

| | | | |
|---|---|---|---|
| 4,906,927 | A | 3/1990 | Urata et al. |
| 5,270,647 | A * | 12/1993 | Beissner .............. G01N 27/902 |
| | | | 324/228 |
| 10,060,881 | B2 * | 8/2018 | Estevez .................. G01N 27/82 |
| 2017/0138217 | A1 * | 5/2017 | Schwarz ............ G01N 15/1031 |
| 2019/0011591 | A1 | 1/2019 | Takahashi et al. |

FOREIGN PATENT DOCUMENTS

| | | |
|---|---|---|
| JP | 7-72263 A | 3/1995 |
| JP | 7-318536 A | 12/1995 |
| JP | 2002-257789 A | 9/2002 |
| JP | 2018-169392 A | 11/2018 |

* cited by examiner

METHOD AND DEVICE FOR DETECTING METAL RESIDUE IN ELECTRIC-RESISTANCE-WELDED STEEL PIPE

TECHNICAL FIELD OF THE INVENTION

The present invention relates to a method and a device for detecting a metal residue such as a bead scrap present in an electric-resistance-welded steel pipe such as an electric-resistance-welded pipe.

Priority is claimed on Japanese Patent Application No. 2018-060523, filed Mar. 27, 2018, the content of which is incorporated herein by reference.

RELATED ART

An electric-resistance-welded pipe (hereinafter, simply referred to as the "welded pipe" in some cases) is manufactured by forming a steel sheet coil of carbon steel, low-alloy steel, or stainless steel in a tubular shape and then welding the steel sheet coil by electromagnetic induction or direct energization. At this time, in a welded part, bulging beads are formed on the inner and outer surfaces of a welded pipe, and thus the bead is removed by cutting after welding. However, there is a case where, particularly, the bead on the inner surface side of the welded pipe is not completely cut. Alternately, there is a case where the bead is cut, but not discharged to the outside of the welded pipe by air blowing or the like and remains in the welded pipe as a bead scrap. The welded pipe in this state being shipped as a product is a problem, and thus it is necessary to detect and remove the bead scrap remaining in the welded pipe before shipment.

In the related art, as a method for detecting a bead scrap remaining in a welded pipe, a variety of methods such as an optical method, a microwave method, and an electromagnetic method have been proposed.

The optical detection method is a method in which, for example, the inside of a welded pipe is captured using a camera disposed near an end of the pipe, thereby detecting a bead scrap. In this method, it is difficult to capture, particularly, a center portion in the longitudinal direction of a small-diameter curved welded pipe, and thus it is difficult to detect a bead scrap remaining in this portion. In addition, in order to put all of the inside of the welded pipe into the camera view, it is necessary to dispose the camera such that the visual axis of the camera is along the pipe axis of the welded pipe, and thus the method is inappropriate for detection while the welded pipe is transported in the longitudinal direction.

The microwave detection method is a method in which, for example, as described in Patent Document 1, a microwave is made incident on one pipe end of a welded pipe and a bead scrap is detected by the frequency modulation or propagation damping of the microwave that has propagated up to the other pipe end. In the microwave detection method as well, similar to the optical detection method, it is necessary to dispose a transmitter or a receiver of the microwave along the pipe axis of the welded pipe, and thus the method is inappropriate for detection while the welded pipe is transported in the longitudinal direction. In addition, the amount of the microwave damped varies depending on the length of the welded pipe, and thus, in the case of inspecting welded pipes having different lengths, an effort such as the necessity for knowing the lengths of the welded pipes in advance is required.

As the electromagnetic detection method, for example, methods described in Patent Documents 2 and 3 are proposed.

The method described in Patent Document 2 is a method in which, as a method for inspecting a flaw, a well-known eddy-current flaw detection method is used for the detection of a bead scrap. Specifically, in the method described in Patent Document 2, a metal pipe is inserted into a magnetic coil and an eddy-current detecting coil. In addition, the method described in Patent Document 2 is a method in which an alternating voltage is supplied to the eddy-current detecting coil to induce an eddy current in a state in which the metal pipe is magnetically saturated by the magnetic coil and magnetized to an extent that a bead scrap present in the metal pipe is not magnetically saturated, and a change in the alternating voltage attributed to an impedance change of the eddy-current detecting coil is measured, thereby detecting the bead scrap.

In addition, the method described in Patent Document 3 is a method similar to the method described in Patent Document 2, but is different from the method described in Patent Document 2 in terms of the fact that an eddy-current detecting coil for flaw detection and an eddy-current detecting coil for bead scrap detection are provided, and the coil width of the eddy-current detecting coil for bead scrap detection is set to be larger than the coil width of the eddy-current detecting coil for flaw detection, thereby detecting a flaw and a bead scrap and enabling the discrimination of both.

The methods described in Patent Documents 2 and 3 are all a method in which a bead scrap is detected using the eddy-current flaw detection method, and the impedance change of the eddy-current detecting coil in the case of supplying an alternating voltage (applying an alternating current) to the eddy-current detecting coil is used for the detection of a bead scrap. Specifically, the methods described in Patent Documents 2 and 3 are a method in which the eddy-current flaw detection method is used, and thus a signal component synchronized with the frequency of the alternating current applied to the eddy-current detecting coil is selectively extracted (synchronously detected) from an output signal of the eddy-current detecting coil and plotted in an impedance plane. The eddy current generated in the metal pipe is an alternating current and is affected by the skin effect, and thus the density of the eddy current is highest on the outer surface of the metal pipe and is damped toward the inner surface of the metal pipe. Therefore, regarding the detection of a bead scrap present inside of the inner surface of the metal pipe, a method in which the eddy-current flaw detection method is used as described in Patent Documents 2 and 3 is considered as, inherently, a low-sensitivity method.

PRIOR ART DOCUMENT

Patent Document

[Patent Document 1] Japanese Unexamined Patent Application, First Publication No. H4-215046
[Patent Document 2] Japanese Unexamined Patent Application, First Publication No. H7-72263
[Patent Document 3] Japanese Unexamined Patent Application, First Publication No. H7-318536

DISCLOSURE OF THE INVENTION

Problems to be Solved by the Invention

The present invention has been made in order to solve the above-described problem of the related art, and an object of the present invention is to provide a method and a device for highly sensitively detecting a metal residue such as a bead scrap present in an electric-resistance-welded steel pipe (hereinafter, simply referred to as the "metal pipe" in some cases) such as an electric-resistance-welded pipe.

Means for Solving the Problem

The present inventors carried out intensive studies regarding a method for detecting a metal residue present in a metal pipe in order to attain the above-described object. As a result, the present inventors found that, when a detecting coil into which the metal pipe is inserted is not used for the measurement of an impedance change as in the eddy-current flaw detection method, but used to catch a cross-sectional area change of a metal passing through the detecting coil, it is possible to highly sensitively detect a metal residue present in the metal pipe and completed the present invention.

The present invention has been made in consideration of the above-described circumstance and employed the following aspects.

(1) An aspect of the present invention is a method for detecting a metal residue present in an electric-resistance-welded steel pipe, the method including a first step of inserting the electric-resistance-welded steel pipe into an exciting coil while relatively moving the electric-resistance-welded steel pipe in a longitudinal direction and magnetizing the electric-resistance-welded steel pipe using a direct current at a field intensity capable of magnetizing the electric-resistance-welded steel pipe and the metal residue up to a magnetic saturation state by the exciting coil and a second step of inserting the electric-resistance-welded steel pipe into a detecting coil while relatively moving the electric-resistance-welded steel pipe in the longitudinal direction, detecting an induced electromotive force generated in the detecting coil by a change in a magnetic flux caused by the direct-current magnetization by the exciting coil in the first step as an output signal of the detecting coil, and detecting the metal residue present in the electric-resistance-welded steel pipe on the basis of the output signal of the detecting coil.

According to the aspect described in (1), in a case where the metal residue is not present in the metal pipe, the metal pipe is magnetized using a direct current up to a magnetic saturation state by the exciting coil by executing the first step. Therefore, in the second step, the magnetic flux distribution in a portion of the metal pipe inserted into the detecting coil becomes substantially uniform in a cross section orthogonal to the longitudinal direction of the metal pipe. That is, a magnetic flux $\phi p$ proportional to the product of the saturated magnetic flux density and the cross-sectional area of the metal pipe is considered to pass through the inside of the detecting coil. When the cross-sectional area of the metal pipe is substantially constant in the longitudinal direction, the relative movement in the longitudinal direction of the metal pipe (relative movement relative to the exciting coil and the detecting coil) rarely causes a change in the magnetic flux $\phi p$. Therefore, in the second step, an induced electromotive force is rarely generated in the detecting coil, and the output signal of the detecting coil becomes close to zero.

On the other hand, in a case where the metal residue is present in the metal pipe, not only the metal pipe but also the metal residue are magnetized using a direct current up to a magnetic saturation state by the exciting coil by executing the first step. Therefore, a magnetic flux $\phi b$ proportional to the product of the saturated magnetic flux density and the cross-sectional area of the metal residue is also generated in the metal residue. In the second step, when the front end (an end on the downstream side in the relative movement direction of a welded pipe) of the metal residue is inserted into the detecting coil in association with the relative movement (relative movement relative to the exciting coil and the detecting coil) of the metal pipe, the magnetic flux increases from the magnetic flux $\phi p$ by the magnetic flux $\phi b$ of the metal residue, whereby an induced electromotive force is generated in the detecting coil. In addition, when the rear end (an end on the upstream side in the relative movement direction of the welded pipe) of the metal residue passes through the detecting coil, the magnetic flux decreases from the magnetic flux $\phi p$+the magnetic flux $\phi b$ by the magnetic flux $\phi b$ of the metal residue, whereby an induced electromotive force is generated in the detecting coil. Therefore, in the second step, when the induced electromotive force generated in the detecting coil is detected as an output signal of the detecting coil, it is possible to highly sensitively detect the metal residue present in the metal pipe on the basis of the output signal of the detecting coil.

According to the aspect described in (1), it is possible to highly sensitively detect the metal residue present in the metal pipe. Furthermore, as described in Patent Document 2, there is an advantage that a delicate adjustment for carrying out magnetization to an extent that the metal pipe is magnetically saturated, but the metal residue present in the metal pipe is not magnetically saturated is not necessary.

(2) In the method for detecting a metal residue present in an electric-resistance-welded steel pipe according to (1), in the second step, an alternating current may not be applied to the detecting coil.

In the case of the aspect described in (2), unlike Patent Documents 2 and 3, the detecting coil is not used for eddy-current flaw detection, and it is considered that the detecting coil is simply used only to monitor the induced electromotive force generated by the magnetic flux of the metal residue.

As the aspect in which an alternating current is not applied to the detecting coil, an aspect in which an alternating-current power supply connected to the detecting coil is not prepared and an aspect in which an alternating-current power supply is used, but the alternating-current power supply is not connected to the detecting coil at all times at the time of executing the second step.

(3) In the method for detecting a metal residue present in an electric-resistance-welded steel pipe according to (1), the second step may include an alternating-current application step of applying an alternating current having a predetermined frequency to the detecting coil, a flaw detection step of detecting a flaw present in the electric-resistance-welded steel pipe on the basis of a signal component obtained by synchronous detection with the frequency of the alternating current, in the output signal of the detecting coil to which the alternating current has been applied, and a metal residue detection step of detecting the metal residue present in the electric-resistance-welded steel pipe on the basis of a signal component permeating a low pass filter having the frequency of the alternating current as a cutoff frequency, in the output signal of the detecting coil to which the alternating current has been applied.

According to the aspect described in (3), the detecting coil can be used to detect the metal residue and also can be used for ordinary eddy-current flaw detection for flaw detection. That is, when the alternating-current application step of applying an alternating current having a predetermined frequency to the detecting coil is executed, in the flaw detection step, ordinary eddy-current flaw detection using, in the output signal of the detecting coil, the signal component obtained by the synchronous detection with the frequency of the applied alternating current becomes possible. It is considered that, in the signal component permeating the low pass filter having the frequency of the applied alternating current as a cutoff frequency in the output signal of the detecting coil, the induced electromotive force generated by the magnetic flux of the metal residue is dominantly included. Therefore, in the metal residue detection step, it is possible to detect the metal residue in the same manner as in the aspect described in (2) in which an alternating current is not applied to the detecting coil using the signal component permeating the low pass filter in the output signal of the detecting coil.

In the aspect described in (3), the same output signal of the detecting coil is branched into two flows in a state in which the alternating current is applied to the detecting coil, one flow is synchronously detected and used for flaw detection, and the other flow is permeated through the low pass filter and used for the detection of the metal residue.

However, the aspect in which the detecting coil is used to detect the metal residue and is also used for ordinary eddy-current flaw detection for flaw detection is not limited to the aspect described in (3), and the turning of the application of an alternating current to the detecting coil on and off can also be considered.

(4) In the method for detecting a metal residue present in an electric-resistance-welded steel pipe according to (1), the second step may include a flaw detection step of applying an alternating current having a predetermined frequency to the detecting coil and detecting a flaw present in the electric-resistance-welded steel pipe on the basis of a signal component obtained by synchronous detection with the frequency of the alternating current, in the output signal of the detecting coil to which the alternating current has been applied, and a metal residue detection step of stopping application of the alternating current having a predetermined frequency to the detecting coil and detecting the metal residue present in the electric-resistance-welded steel pipe on the basis of the output signal of the detecting coil to which the application of the alternating current is stopped.

According to the aspect described in (4), in the flaw detection step, an alternating current having a predetermined frequency is applied to the detecting coil (the application is turned on), whereby ordinary eddy-current flaw detection using, in the output signal of the detecting coil, the signal component obtained by the synchronous detection with the frequency of the applied alternating current becomes possible. In the metal residue detection step, the application of the alternating current having a predetermined frequency to the detecting coil is stopped (the application is turned off), whereby, similar to the aspect described in (2), the detecting coil is simply used only to monitor the induced electromotive force generated by the magnetic flux of the metal residue, and it is possible to detect the metal residue on the basis of the output signal of the detecting coil.

In the aspect described in (4), the turning of the application of the alternating current to the detecting coil on and off needs to be cyclically repeated. As long as the set repetition cycle is not too long, it is possible to detect both a flaw and the metal residue with no misses.

In the invention, in a case where only one detecting coil is disposed, there is a concern that the ratio (S/N ratio) of a signal component generated due to the metal residue to, in the output signal of the detecting coil, a noise signal component generated due to deviation between the central axis of the metal pipe and the central axis of the detecting coil caused by the vibration or the like of the metal pipe may be small and it may not be possible to precisely detect the metal residue.

In order to avoid the above-described problem, the following aspects were employed.

(5) In the method for detecting a metal residue present in an electric-resistance-welded steel pipe according to (1), it is preferable that a plurality of the detecting coils is disposed in the longitudinal direction of the electric-resistance-welded steel pipe and the second step includes a step of averaging the output signals of the plurality of detecting coils output at the same time to compute a first signal (hereinafter, this step will be appropriately referred to as the "first step"), a step of subtracting the first signal from the output signals of the plurality of detecting coils output at the same time to compute second signals respectively corresponding to the plurality of detecting coils (hereinafter, this step will be appropriately referred to as the "second step"), a step of shifting horizontal axes of the plurality of second signals by a separation distance between the plurality of detecting coils and adding the plurality of shifted second signals to each other to compute a third signal (hereinafter, this step will be appropriately referred to as the "third step"), and a step of detecting the metal residue present in the electric-resistance-welded steel pipe on the basis of the third signal (hereinafter, this step will be appropriately referred to as the "fourth step"). Hereinafter, this preferred method will be appropriately referred to as the "first preferred method". The horizontal axes indicate distances from the beginning of making the electric-resistance-welded steel pipe.

According to the first preferred method, in the third signal computed by the third step, the S/N ratio of the signal component generated due to the metal residue increases, and it is possible to precisely detect the metal residue.

In a case where the second step is the aspect described in (2), the "output signals of the plurality of detecting coils output at the same time" in the first step of the first preferred method refer, literally, to output signals of the plurality of detecting coils output at the same time. In addition, in a case where the second step is the aspect described in (3), the "output signals of the plurality of detecting coils output at the same time" in the first step of the first preferred method refer to, among the output signals of the plurality of detecting coils output at the same time, a signal component permeating the low pass filter. Furthermore, in a case where the second step is the aspect described in (4), the "output signals of the plurality of detecting coils output at the same time" in the first step of the first preferred method refer to output signals of the plurality of detecting coils, to which the application of the alternating current has been stopped, output at the same time.

In addition, in order to avoid the above-described problem, the method is not limited to a case where all of the first to fourth steps are executed in this order as in the first preferred method and may be a method in which the third step is omitted.

That is, in order to avoid the above-described problem, the following aspects were employed.

(6) In the method for detecting a metal residue present in an electric-resistance-welded steel pipe according to (1), it is preferable that a plurality of the detecting coils is disposed in the longitudinal direction of the electric-resistance-welded steel pipe and the second step includes a step of averaging the output signals of the plurality of detecting coils output at the same time to compute a first signal (the same step as the first step), a step of subtracting the first signal from the output signals of the plurality of detecting coils output at the same time to compute second signals respectively corresponding to the plurality of detecting coils (the same step as the second step), and a step of detecting the metal residue present in the electric-resistance-welded steel pipe on the basis of at least any one of the plurality of second signals (the same step as the fourth step). Hereinafter, this preferred method will be appropriately referred to as the "second preferred method".

According to the second preferred method, in the second signal, the S/N ratio of the signal component generated due to the metal residue increases, and it is possible to precisely detect the metal residue.

In a case where the second step is the aspect described in (2), the "output signals of the plurality of detecting coils output at the same time" in the step of computing the first signal of the second preferred method refer, literally, to output signals of the plurality of detecting coils output at the same time. In addition, in a case where the second step is the aspect described in (3), the "output signals of the plurality of detecting coils output at the same time" in the step of computing the first signal of the second preferred method refer to, among the output signals of the plurality of detecting coils output at the same time, a signal component permeating the low pass filter. Furthermore, in a case where the second step is the aspect described in (4), the "output signals of the plurality of detecting coils output at the same time" in the step of computing the first signal of the second preferred method refer to output signals of the plurality of detecting coils, to which the application of the alternating current has been stopped, output at the same time.

In addition, in order to avoid the above-described problem, the method is not limited to a case where all of the first to fourth steps are executed in this order as in the first preferred method and may be a method in which the step relating to the third step is first executed and then the step relating to the fourth step is executed.

In order to avoid the above-described problem, the following aspects were employed.

(7) In the method for detecting a metal residue present in an electric-resistance-welded steel pipe according to (1), it is preferable that a plurality of the detecting coils is disposed in the longitudinal direction of the electric-resistance-welded steel pipe and the second step includes a step of shifting horizontal axes of the output signals of the plurality of detecting coils by a separation distance between the plurality of detecting coils and adding the plurality of shifted output signals to each other to compute a fourth signal (a step relating to the third step) and a step of detecting the metal residue present in the electric-resistance-welded steel pipe on the basis of the fourth signal (a step relating to the fourth step). Hereinafter, this preferred method will be appropriately referred to as the "third preferred method". The horizontal axes indicate distances from the beginning of making the electric-resistance-welded steel pipe.

According to the third preferred method, in the fourth signal, the S/N ratio of the signal component generated due to the metal residue increases, and it is possible to precisely detect the metal residue.

In a case where the second step is the aspect described in (2), the "output signals of the plurality of detecting coils" in the step of computing the fourth signal of the third preferred method refer, literally, to output signals of the plurality of detecting coils output at the same time. In addition, in a case where the second step is the aspect described in (2), the "output signals of the plurality of detecting coils" in the step of computing the fourth signal of the third preferred method refer to, among the output signals of the plurality of detecting coils output at the same time, a signal component permeating the low pass filter. Furthermore, in a case where the second step is the aspect described in (4), the "output signals of the plurality of detecting coils" in the step of computing the fourth signal of the third preferred method refer to output signals of the plurality of detecting coils, to which the application of the alternating current has been stopped, output at the same time.

(8) In the method for detecting a metal residue present in an electric-resistance-welded steel pipe according to any one of (1) to (7), the metal residue present in the electric-resistance-welded steel pipe may be detected by a yoke member having a first opening part which is located on one end side along the longitudinal direction of the electric-resistance-welded steel pipe and into which the electric-resistance-welded steel pipe is inserted and a second opening part which is located on the other end side along the longitudinal direction of the electric-resistance-welded steel pipe and into which the electric-resistance-welded steel pipe is inserted, having an outer shape substantially axisymmetric with respect to an axis passing through the first opening part and the second opening part, and surrounding the exciting coil and the detecting coil.

According to the aspect described in (8), it is possible to reduce a dead zone in an end portion of a metal pipe in the longitudinal direction.

(9) Another aspect of the present invention is a device for detecting a metal residue present in an electric-resistance-welded steel pipe, the device including an exciting coil into which the electric-resistance-welded steel pipe relatively moving in a longitudinal direction is inserted and which magnetizes the electric-resistance-welded steel pipe using a direct current at a field intensity capable of magnetizing the electric-resistance-welded steel pipe and the metal residue up to a magnetic saturation state, a detecting coil into which the electric-resistance-welded steel pipe relatively moving in the longitudinal direction is inserted and which detects and outputs an induced electromotive force generated by a change in a magnetic flux caused by direct-current magnetization by the exciting coil, and a detector for detecting the metal residue present in the electric-resistance-welded steel pipe on the basis of an output signal of the detecting coil.

(10) In the device for detecting a metal residue present in an electric-resistance-welded steel pipe according to (9), a plurality of the detecting coils is disposed in the longitudinal direction of the electric-resistance-welded steel pipe, and the detector includes a first signal computation unit configured to average the output signals of the plurality of detecting coils output at the same time to compute a first signal, a second signal computation unit configured to subtract the first signal from the output signals of the plurality of detecting coils output at the same time to compute second signals respectively corresponding to the plurality of detecting coils, a third signal computation unit configured to shift horizontal axes of the plurality of second signals by a separation distance between the plurality of detecting coils and adding the plurality of shifted second signals to each other to compute a third signal, and a first detection unit configured to detect the metal residue present in the electric-resistance-welded steel pipe on the basis of the third signal.

(11) In the device for detecting a metal residue present in an electric-resistance-welded steel pipe according to (9), a plurality of the detecting coils is disposed in the longitudinal direction of the electric-resistance-welded steel pipe, and the detector includes a first signal computation unit configured to average the output signals of the plurality of detecting coils output at the same time to compute a first signal, a second signal computation unit configured to subtract the first signal from the output signals of the plurality of detecting coils output at the same time to compute second signals respectively corresponding to the plurality of detecting coils, and a second detection unit configured to detect the metal residue present in the electric-resistance-welded steel pipe on the basis of at least any one of the plurality of second signals.

(12) In the device for detecting a metal residue present in an electric-resistance-welded steel pipe according to (9), a plurality of the detecting coils is disposed in the longitudinal direction of the electric-resistance-welded steel pipe, and the detector includes a fourth signal computation unit configured to shift horizontal axes of the output signals of the plurality of detecting coils by a separation distance between the plurality of detecting coils and adding the plurality of shifted output signals to each other to compute a fourth signal and a third detection unit configured to detect the metal residue present in the electric-resistance-welded steel pipe on the basis of the fourth signal.

(13) In the device for detecting a metal residue present in an electric-resistance-welded steel pipe according to any one of (9) to (12), the device further includes a yoke member having a first opening part which is located on one end side along the longitudinal direction of the electric-resistance-welded steel pipe and into which the electric-resistance-welded steel pipe is inserted and a second opening part which is located on the other end side along the longitudinal direction of the electric-resistance-welded steel pipe and into which the electric-resistance-welded steel pipe is inserted, having an outer shape substantially axisymmetric with respect to an axis passing through the first opening part and the second opening part, and surrounding the exciting coil and the detecting coil.

Effects of the Invention

According to the present invention, it is possible to highly sensitively detect a metal residue such as a bead scrap present in an electric-resistance-welded steel pipe such as an electric-resistance-welded pipe.

Figure 1A:
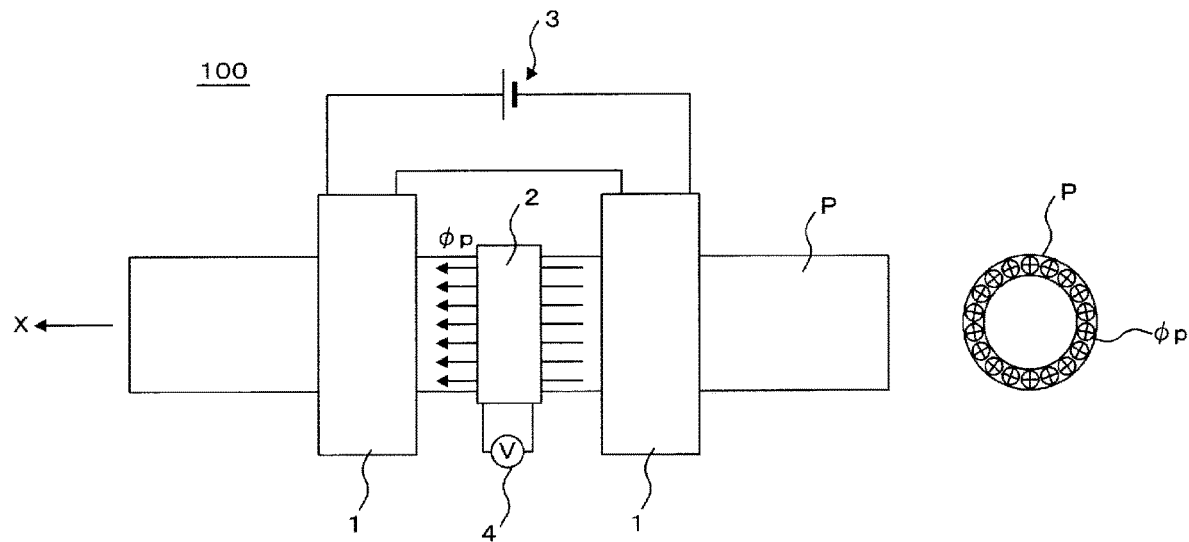
FIG. 1A is a view for describing a detection method according to a first embodiment of the present invention and shows a case where a bead scrap B is not present in a welded pipe P.
Figure 1B:
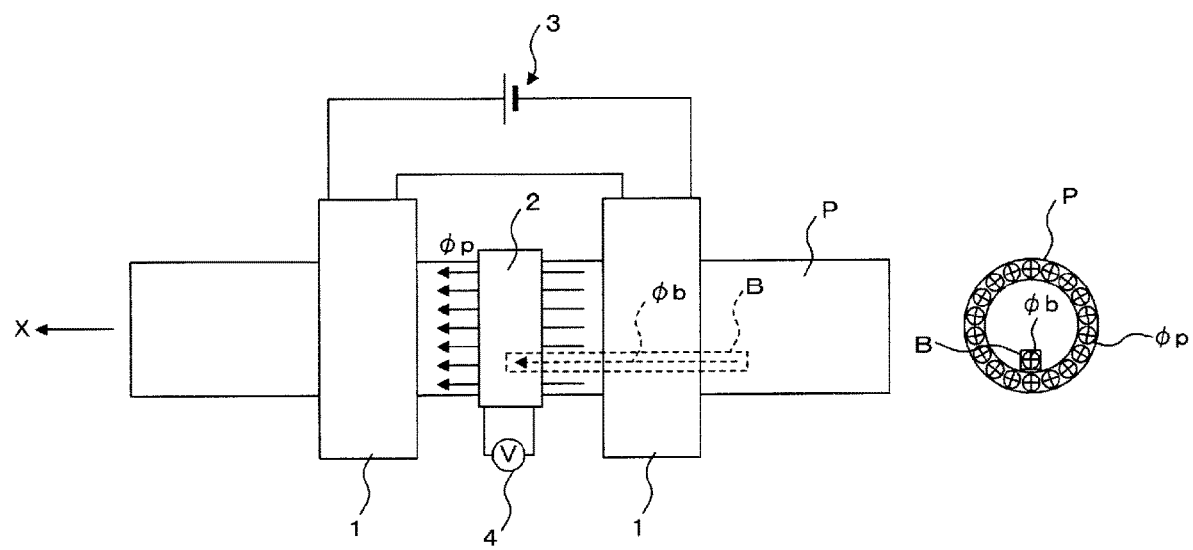
FIG. 1B is a view for describing the detection method according to the same embodiment and shows a case where the bead scrap B is present in the welded pipe P.
Figure 1C:
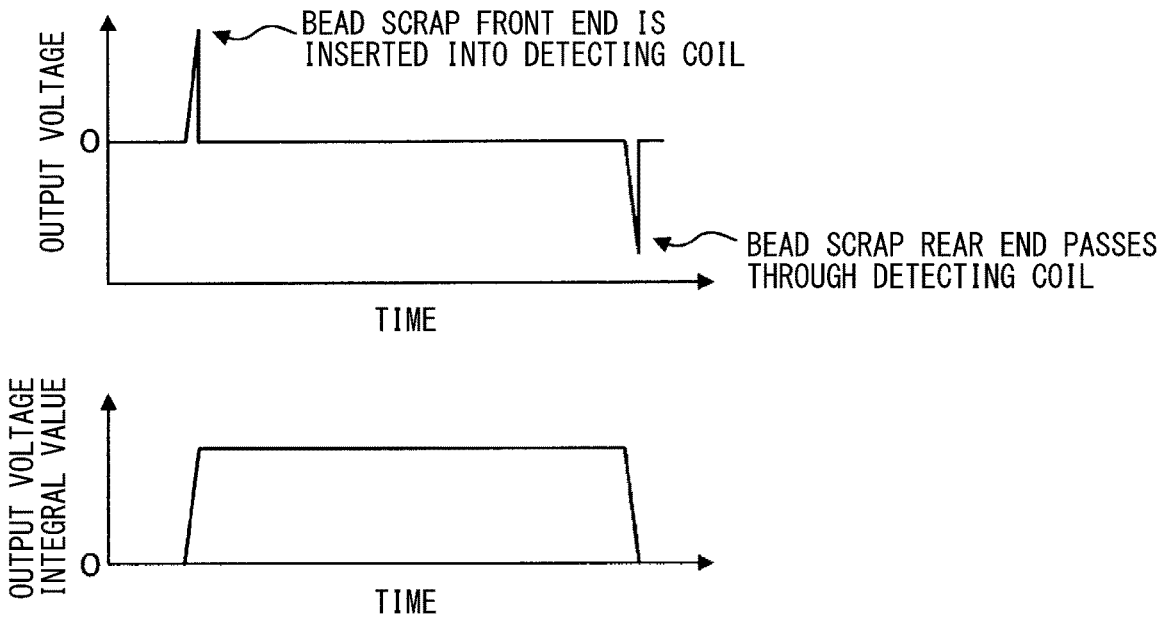

An upper view of FIG. 1C is a view schematically showing an output signal of a detecting coil 2 in the case of FIG. 1B, and a lower view is a view schematically showing a signal obtained by integrating the output signal shown in the upper view.

Figure 2:
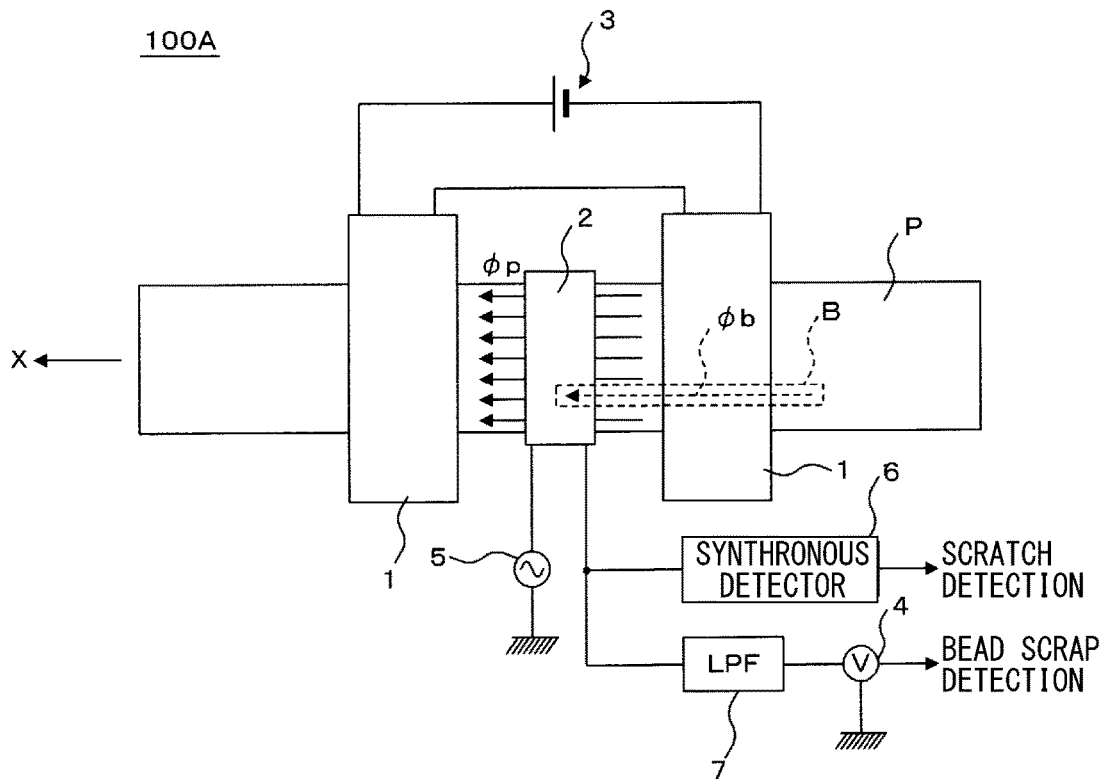

FIG. 2 is a side view for describing a detection method according to a second embodiment of the present invention.

Figure 3:
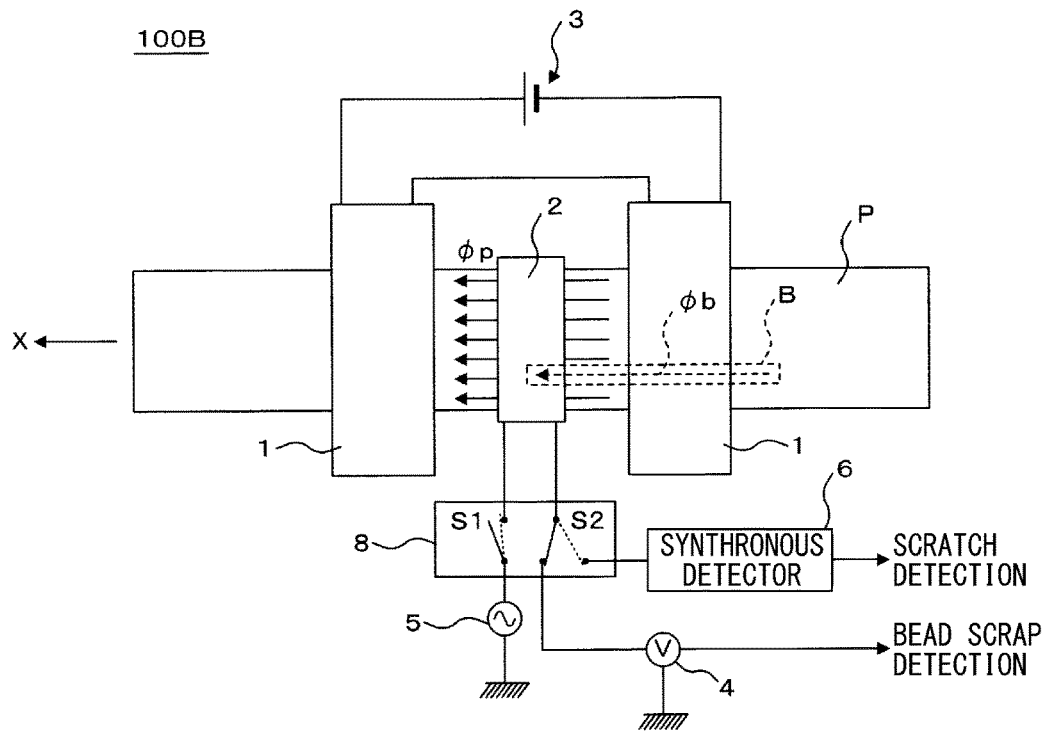

FIG. 3 is a side view for describing a detection method according to a third embodiment of the present invention.

Figure 4:
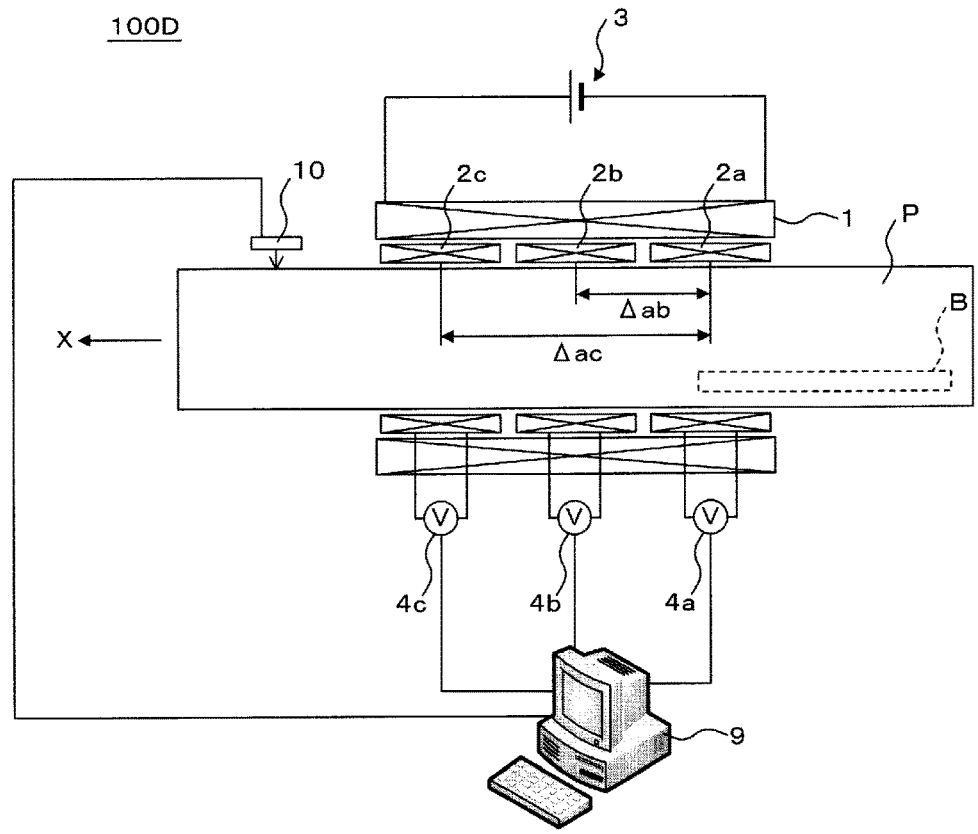

FIG. 4 is a view for describing a first modification example of the detection method according to the first embodiment of the present invention.

Figure 5:
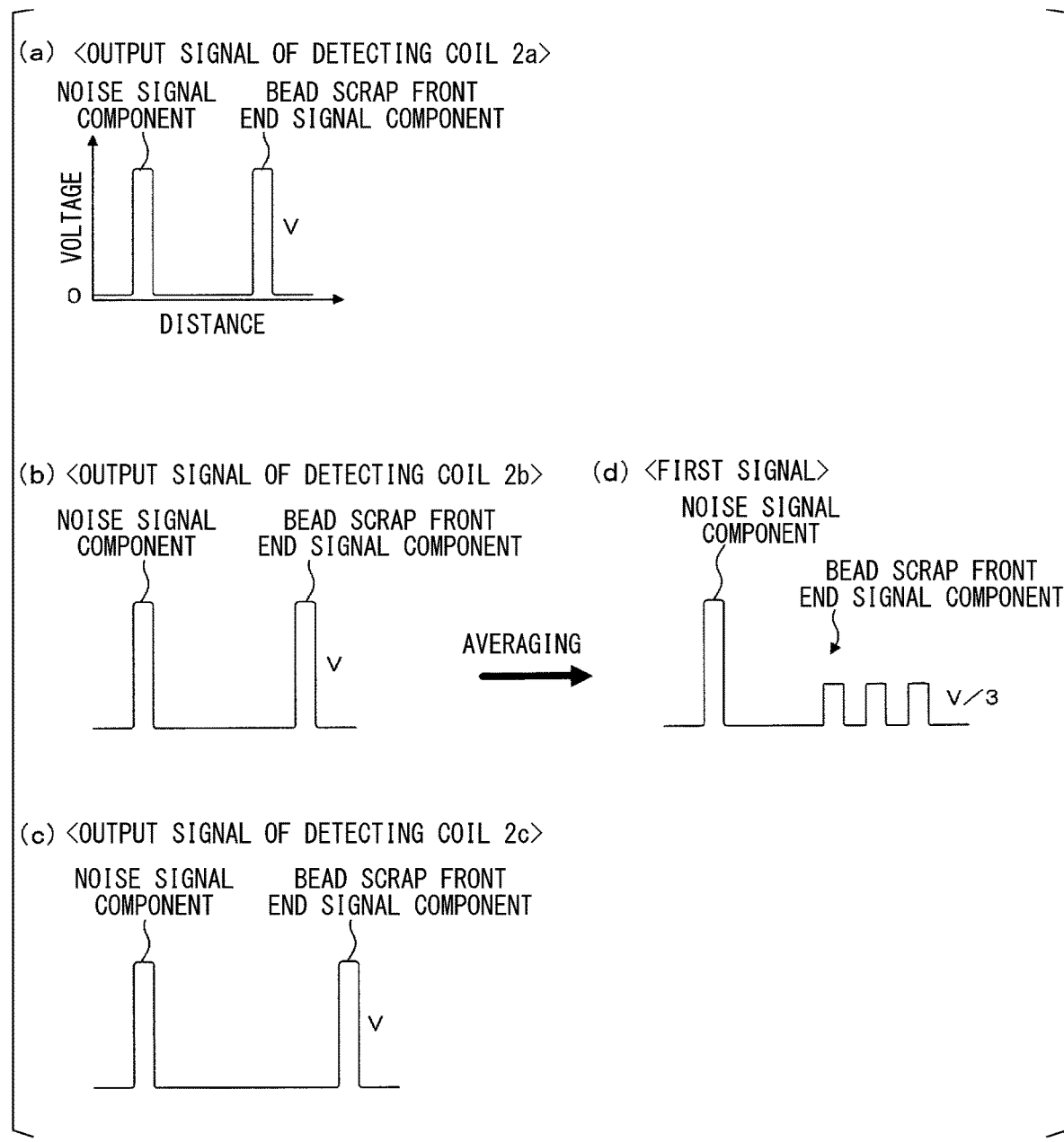

FIG. 5 is a view for schematically describing the content of a first step of the first modification example of the detection method according to the first embodiment of the present invention.

Figure 6:
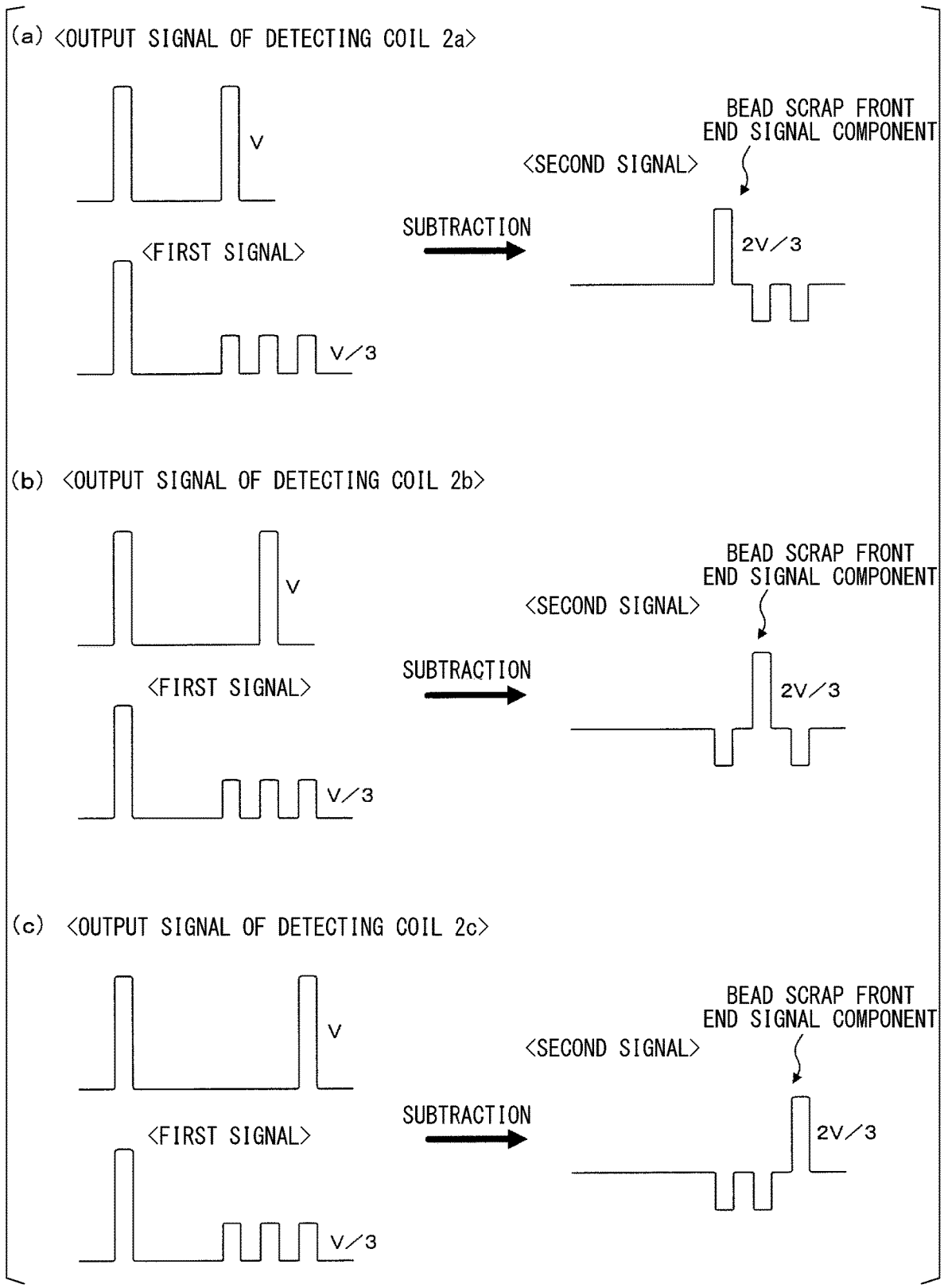

FIG. 6 is a view for schematically describing the content of a second step of the first modification example of the detection method according to the first embodiment of the present invention.

Figure 7:
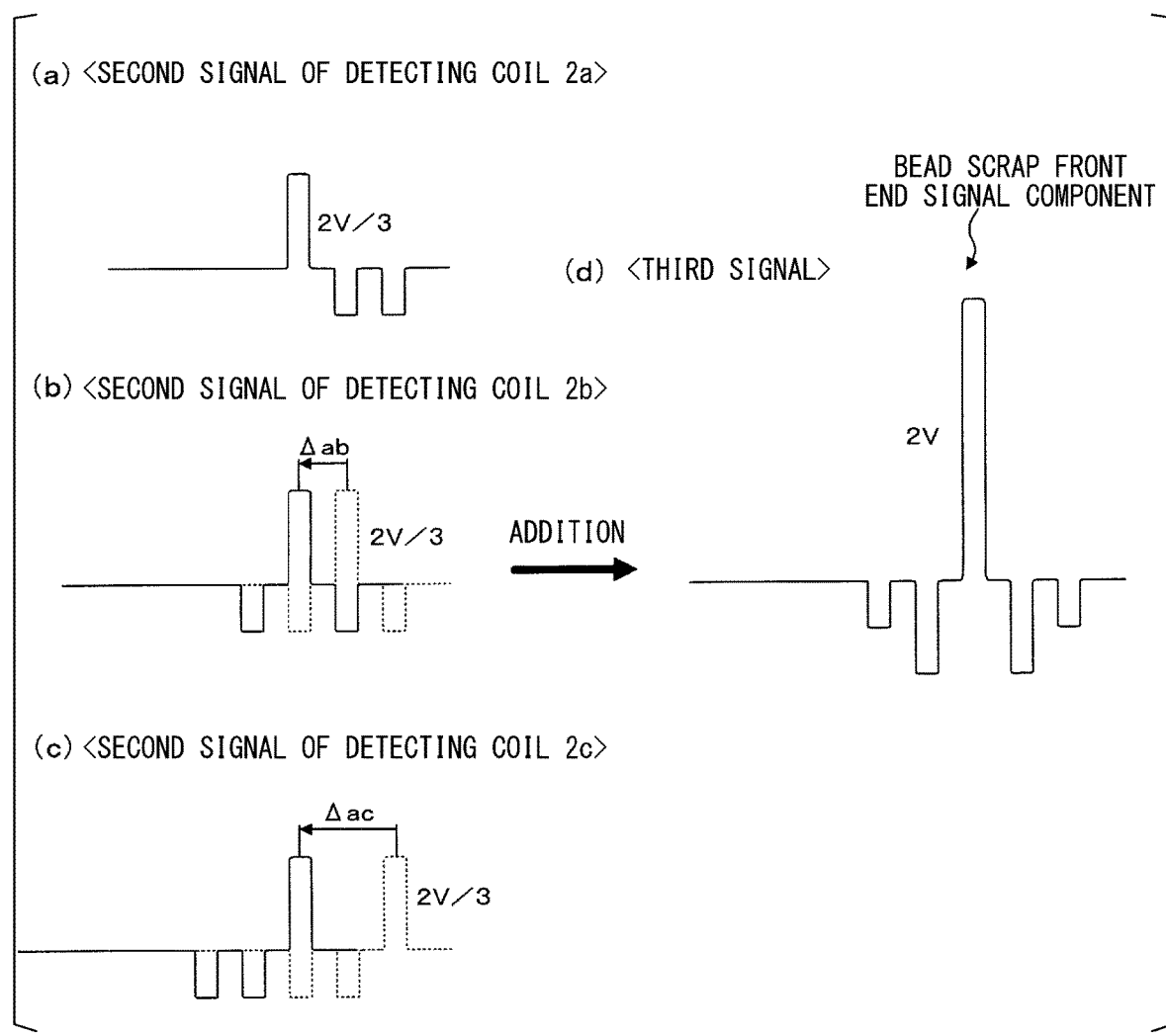

FIG. 7 is a view for schematically describing the content of a third step of the first modification example of the detection method according to the first embodiment of the present invention.

Figure 8:
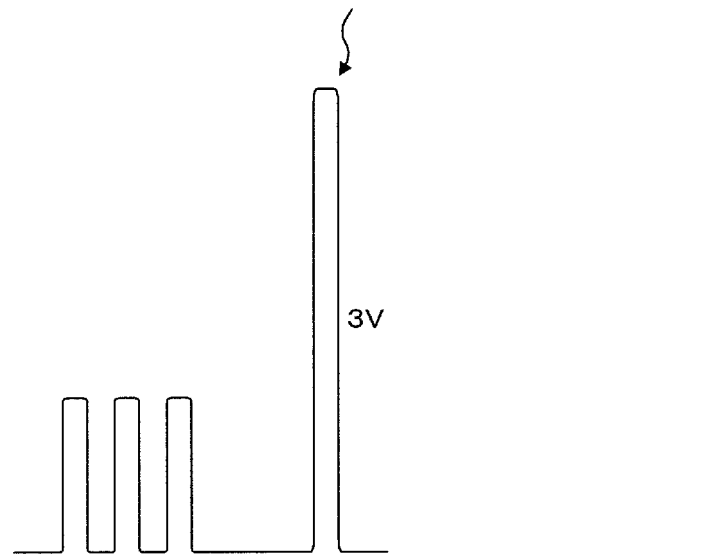

FIG. 8 is a view schematically showing a fourth signal computed in a third modification example of the detection method according to the first embodiment of the present invention.

Figure 9A:
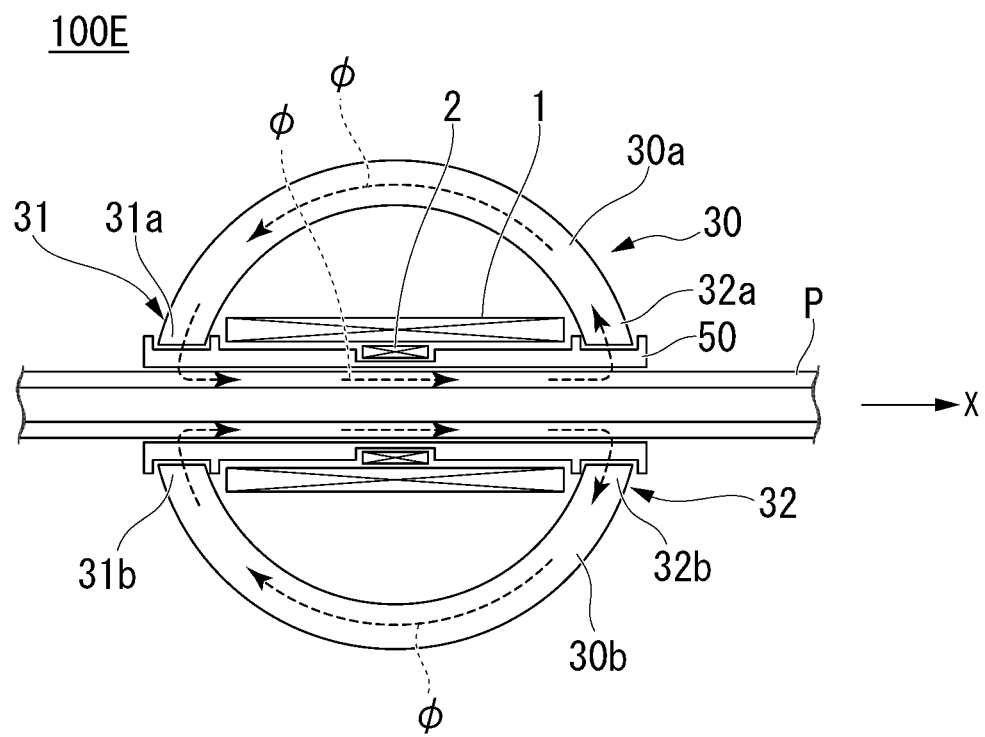

FIG. 9A is a view showing a schematic configuration of a detection device used to execute a detection method of a fourth modification example of the present invention and a cross-sectional view in the case of being seen on a longitudinal section including a central axis line of the welded pipe P.

Figure 9B:
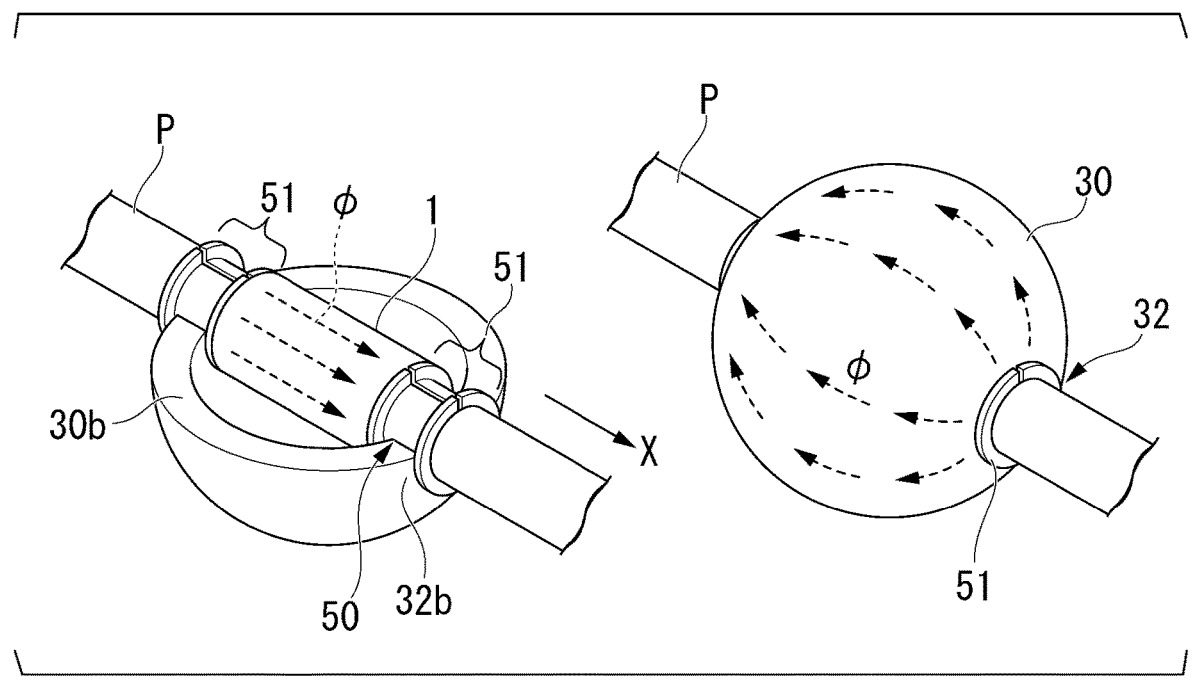

FIG. 9B is a perspective view of FIG. 9A.

Figure 10:
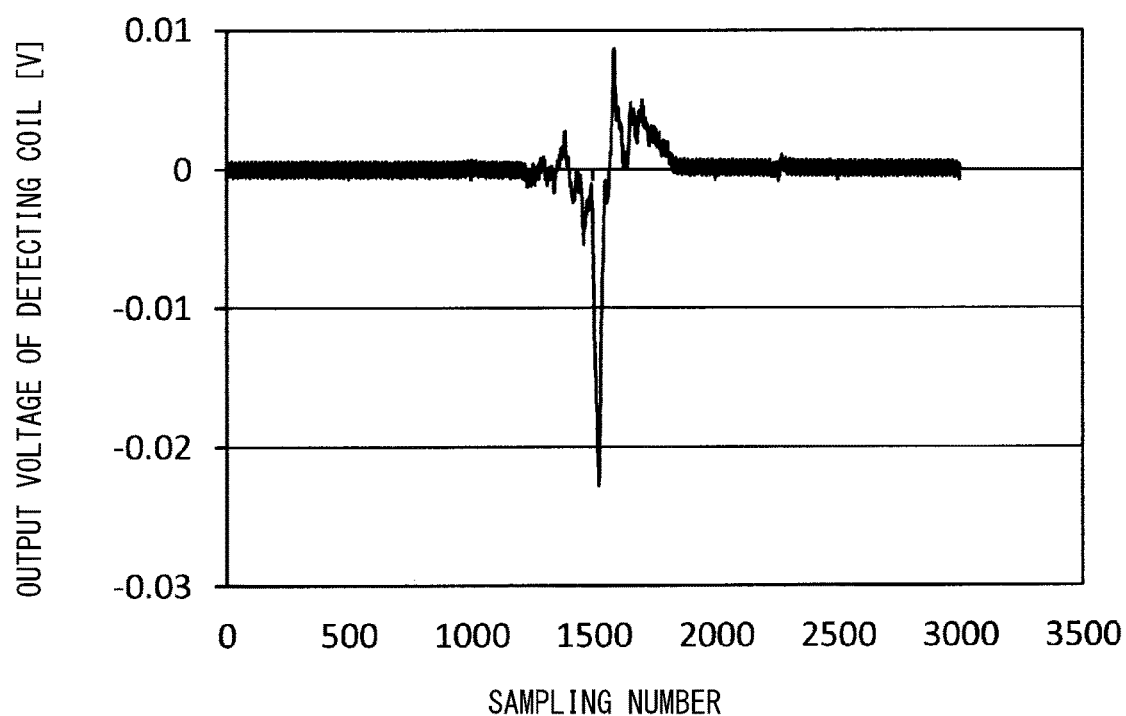

FIG. 10 is a graph showing an example of an output signal of a detecting coil obtained using a detection method according to a fourth modification example shown in FIG. 9A and FIG. 9B.

EMBODIMENTS OF THE INVENTION

Hereinafter, a method for detecting a metal residue in an electric-resistance-welded steel pipe (hereinafter, appropriately, simply referred to as the "detection method") and a device for detecting a metal residue in an electric-resistance-welded steel pipe (hereinafter, appropriately, simply referred to as the "detection device") according to an embodiment of the present invention will be described with appropriate reference to the accompanying drawings. In the present embodiment, the detection method and the detection device will be described using a case where the metal residue is a bead scrap as an example.

Detection methods according to first to third embodiments are included in the scope of the detection method according to the present embodiment. All of the detection methods according to the first to third embodiments include a first step of magnetizing a welded pipe using a direct current and a second step of detecting a bead scrap present in the welded pipe, but the aspect of the second step varies in the respective embodiments. Hereinafter, the detection methods according to the first to third embodiments will be sequentially described.

First Embodiment

FIG. 1A and FIG. 1B are views for describing the detection method according to the first embodiment. The left view of FIG. 1A is a side view schematically showing a magnetic flux distribution in a case where a bead scrap B is not present in a welded pipe P. The right view of FIG. 1A is a view schematically showing a magnetic flux distribution in a cross section of a detecting coil 2 in the left view of FIG. 1A. The left view of FIG. 1B is a side view schematically showing a magnetic flux distribution in a case where the bead scrap B is present in the welded pipe P. The right view of FIG. 1B is a view schematically showing a magnetic flux distribution in a cross section of the detecting coil 2 in the left view of FIG. 1B. The upper view of FIG. 1C is a view schematically showing an output signal of the detecting coil 2 in the case of FIG. 1B, and the lower view of FIG. 1C is a view schematically showing a signal obtained by integrating the output signal shown in the upper view of FIG. 1C.

As shown in FIG. 1A and FIG. 1B, the detection method according to the first embodiment is executed using a detection device 100 according to the first embodiment. The detection device 100 includes an exciting coil 1, a detecting coil 2, and a voltmeter 4 as detector. In addition, the detection device 100 includes a direct-current power supply 3. In an example shown in FIG. 1A and FIG. 1B, the exciting coil 1 is divided into two pieces in the longitudinal direction (X direction) of the welded pipe P, but the configuration is not limited thereto, and it is also possible to employ a configuration in which a single undivided exciting coil is used and the detecting coil 2 is disposed therein. This is also true for a detection device 100A shown in FIG. 2 and a detection device 100B shown in FIG. 3 described below.

In the detection method according to the first embodiment, in the first step, the welded pipe P is relatively moved in the longitudinal direction (in the present embodiment, the welded pipe P is moved relative to the fixed exciting coil 1) and inserted into the exciting coil 1, and the welded pipe P is magnetized in the longitudinal direction using a direct current by the exciting coils 1 at a field intensity capable of magnetizing the welded pipe P and the bead scrap B up to a magnetic saturation state. Specifically, the direct current power supply 3 is connected to the exciting coils 1, and a direct current is applied to the exciting coils 1 from the direct current power supply 3 such that a field intensity determined by a current carried to the exciting coils 1 and the number of turns of the exciting coil 1 reaches a field intensity capable of magnetizing the welded pipe P and the bead scrap B up to a magnetic saturation state. Regarding magnetizing up to a magnetic saturation state, for example, when a hysteresis curve is acquired by imparting a material with one cycle of alternating-current magnetization for 10 seconds or longer, and the slope of the curve at the peak value of the field intensity, that is, the value of relative magnetic permeability exhibits approximately 20 or less, generally, the material is regarded to be in a saturation region. The bead scrap B is present in a state of partially floating from the inner surface of the welded pipe P in some cases, and a direct current is effective for magnetizing the bead scrap B up to a magnetic saturation state. In the case of an alternating current, it is clear that, in an alternating-current magnetic field, due to an influence of an eddy current generate by a temporal change in the magnetic field, a magnetic flux does not easily penetrate the inside of the bead scrap B.

In addition, in the detection method according to the first embodiment, in the second step, the welded pipe P is relatively moved in the longitudinal direction (in the present embodiment, the welded pipe P is moved relative to the fixed detecting coil 2) and inserted into the detecting coil 2, an induced electromotive force generated in the detecting coil 2 by a change in the magnetic flux caused by the direct-current magnetization by the exciting coils 1 in the first step is detected as an output signal of the detecting coil 2, and the bead scrap B present in the welded pipe P is detected on the basis of the output signal of the detecting coil 2. Specifically, the voltmeter 4 is connected to the detecting coil 2, the output voltage of the detecting coil 2 is measured using the voltmeter 4, and the bead scrap B present in the welded pipe P is detected on the basis of this measured output voltage. In the detection method according to the first embodiment, an alternating current is not applied to the detecting coil 2. Specifically, in the detection method according to the first embodiment, an alternating-current power supply 5 connected to the detecting coil 2 as in the detection method according to the second embodiment or the third embodiment described below is not prepared. However, the present invention is not limited thereto, and it is also possible to employ an aspect in which the alternating-current power supply 5 is prepared, but the alternating-current power supply 5 is not connected to the detecting coil 2 at all times at the time of executing the second step.

According to the detection method according to the first embodiment, in a case where the bead scrap B is not present in the welded pipe P as shown in FIG. 1A, the welded pipe P is magnetized using a direct current up to a magnetic saturation state by the exciting coils 1 by executing the first step. Therefore, in the second step, the magnetic flux distribution in a portion of the welded pipe P inserted into the detecting coil 2 becomes substantially uniform in a cross section orthogonal to the longitudinal direction of the welded pipe P. That is, a magnetic flux ϕpp proportional to the product of the saturated magnetic flux density and the cross-sectional area of the welded pipe P is considered to pass through the inside of the detecting coil 2. When the cross-sectional area of the welded pipe P is substantially constant in the longitudinal direction, the relative movement in the longitudinal direction of the welded pipe P (relative movement relative to the exciting coils 1 and the detecting coil 2) rarely causes a change in the magnetic flux ϕpp. Therefore, in the second step, an induced electromotive force is rarely generated in the detecting coil 2, and the output signal of the detecting coil 2 becomes close to zero. That is, the output voltage of the detecting coil 2 measured by the voltmeter 4 becomes close to zero.

On the other hand, in a case where the bead scrap B is present in the welded pipe P as shown in FIG. 1B, not only the welded pipe P but also the bead scrap B are magnetized using a direct current up to a magnetic saturation state by the exciting coils 1 by executing the first step. Therefore, a magnetic flux ϕb proportional to the product of the saturated magnetic flux density and the cross-sectional area of the bead scrap B is also generated in the bead scrap B. In the second step, when the front end (an end on the downstream side in the relative movement direction of the welded pipe P) of the bead scrap B is inserted into the detecting coil 2 in association with the relative movement of the welded pipe P, the magnetic flux increases from the magnetic flux ϕp by the magnetic flux ϕb of the bead scrap B, whereby an induced electromotive force is generated in the detecting coil 2. That is, as shown in the upper view of FIG. 1C, the output voltage of the detecting coil 2 measured by the voltmeter 4 increases in one direction (in an example shown in FIG. 1C, the positive direction).

In addition, when the rear end (an end on the upstream side in the relative movement direction of the welded pipe P) of the bead scrap B passes through the detecting coil 2, the magnetic flux decreases from the magnetic flux ϕp+the magnetic flux ϕb by the magnetic flux (kb of the bead scrap, whereby an induced electromotive force is generated in the detecting coil 2. That is, as shown in the upper view of FIG. 1C, the output voltage of the detecting coil 2 measured by the voltmeter 4 increases in a direction opposite to the above-described direction (in the example shown in FIG. 1C, the negative direction).

Therefore, in the second step, when the induced electromotive force generated in the detecting coil 2 is detected as the output signal of the detecting coil 2, it is possible to highly sensitively detect the bead scrap B present in the welded pipe P on the basis of the output signal of the detecting coil 2. That is, in a case where the output voltage of the detecting coil 2 as shown in the upper view of FIG. 1C is compared with, for example, a predetermined positive or negative threshold value and exceeds the threshold value, it is possible to determine that the bead scrap B is present in the welded pipe P (a place in which the output voltage exceeds the threshold value is determined to be an end portion of the bead scrap B). In addition, in a case where an integral value of the output voltage as shown in the lower view of FIG. 1C is compared with a predetermined threshold value and exceeds the threshold value, it is also possible to determine that the bead scrap B is present in the welded pipe P (a place in which the integral value exceeds the threshold value is determined to be the bead scrap B).

The detecting coil 2 is preferably disposed on the front half side (the downstream side in the relative movement direction of the welded pipe P) of the center portion of the welded pipe P in the longitudinal direction in a range magnetized using a direct current in the first step. When the welded pipe P is inserted into the exciting coil 1, the magnetic flux density distribution of the welded pipe P changes. That is, immediately after the welded pipe P enters the exciting coil 1, the penetration of the magnetic flux is hindered by an eddy current effect (shield effect), but the welded pipe P magnetized using a direct current gets into a magnetic saturation state particularly from the center portion in the longitudinal direction toward the downstream side in the relative movement direction. Therefore, when the detecting coil 2 is disposed in this range put into the magnetic saturation state, it becomes possible to highly sensitively detect the bead scrap B. This is also true for the second embodiment and the third embodiment.

According to the detection method according to the first embodiment, it is possible to highly sensitively detect the bead scrap B present in the welded pipe P. Furthermore, it is possible to omit a delicate adjustment which is required in Patent Document 2. That is, it is possible to omit a delicate adjustment for carrying out magnetization to an extent that the welded pipe P is magnetically saturated but the bead scrap B present in the welded pipe P is not magnetically saturated.

Second Embodiment

FIG. 2 is a side view for describing the detection method according to the second embodiment.

As shown in FIG. 2, the detection method according to the second embodiment is executed using a detection device 100A according to the second embodiment. The detection device 100A includes the exciting coils 1, the detecting coil 2, the voltmeter 4 as detector, and a low pass filter (LPF) 7. In addition, the detection device 100A includes the direct-current power supply 3, an alternating-current power supply 5, and a synchronous detector 6.

The detection method according to the second embodiment also includes the same first step as in the detection method according to the first embodiment, but is different from the detection method according to the first embodiment in terms of the aspect of the second step. In the detection method according to the second embodiment, the detecting coil 2 is used to detect the bead scrap B and is also used for ordinary eddy-current flaw detection for flaw detection.

The second step of the detection method according to the second embodiment includes an alternating-current application step, a flaw detection step, and a bead scrap detection step (metal residue detection step).

In the alternating-current application step, an alternating current having a predetermined frequency is applied to the detecting coil 2 from the alternating-current power supply 5. An output signal of the detecting coil 2 to which the alternating current is applied is branched into two flows, one flow is input to the synchronous detector 6, and the other flow is input to the low pass filter (LPF) 7.

In the flaw detection step, a flaw present in the welded pipe P is detected on the basis of, in the output signal of the detecting coil 2 to which an alternating current has been applied, a signal component obtained by the synchronous detection by the synchronous detector 6 with the frequency of the alternating current.

In the bead scrap detection step, the bead scrap B present in the welded pipe P is detected on the basis of, in the output signal of the detecting coil 2 to which the alternating current has been applied, a signal component permeating the low pass filter 7 having the frequency of the alternating current as a cutoff frequency. Specifically, the voltmeter 4 is connected to the low pass filter 7, the voltage of the signal component permeating the low pass filter 7 is measured by the voltmeter 4, and the bead scrap B present in the welded pipe P is detected on the basis of the measured voltage. A method for detecting the bead scrap B on the basis of the voltage is the same as the case of the first embodiment described with reference to FIG. 1C and thus will not be described again.

According to the detection method according to the second embodiment, the alternating-current application step of applying an alternating current having a predetermined frequency to the detecting coil 2 is executed, whereby, in the flaw detection step, ordinary eddy-current flaw detection using, in the output signal of the detecting coil 2, the signal component obtained by the synchronous detection with the frequency of the applied alternating current becomes possible. It is considered that, in the signal component permeating the low pass filter 7 having the frequency of the applied alternating current as a cutoff frequency in the output signal of the detecting coil 2, the induced electromotive force generated by the magnetic flux (kb of the bead scrap B is dominantly included. Therefore, in the bead scrap detection step, it is possible to detect the bead scrap B in the same manner as in the detection method according to the first embodiment in which an alternating current is not applied to the detecting coil 2 using the signal component permeating the low pass filter 7 in the output signal of the detecting coil 2.

Third Embodiment

FIG. 3 is a side view for describing the detection method according to the third embodiment.

As shown in FIG. 3, the detection method according to the third embodiment is executed using a detection device 100B according to the third embodiment. The detection device 100B includes the exciting coils 1, the detecting coil 2, and the voltmeter 4 as detector. In addition, the detection device 100B includes the direct-current power supply 3, the alternating-current power supply 5, the synchronous detector 6, and a switching circuit 8.

The detection method according to the third embodiment also includes the same first step as in the detection methods according to the first embodiment and the second embodiment, but is different from the detection method according to the first embodiment and the second embodiment in terms of the aspect of the second step.

In the detection method according to the third embodiment, unlike the detection method according to the first embodiment, the detecting coil 2 is used to detect the bead scrap B and is also used for ordinary eddy-current flaw detection for flaw detection.

In addition, in the detection method according to the third embodiment, unlike the detection method according to the second embodiment, an alternating current is not continuously applied to the detecting coil 2 from the alternating-current power supply 5, but the application of an alternating current to the detecting coil 2 from the alternating-current power supply 5 is turned on and off using the switching circuit 8.

The second step of the detection method according to the third embodiment includes a flaw detection step and a bead scrap detection step (metal residue detection step).

In the flaw detection step, switches S1 and S2 provided in the switching circuit 8 each reach states indicated by dotted lines in FIG. 3. That is, a state in which the alternating-current power supply 5 and the detecting coil 2 are connected to each other and the detecting coil 2 and the synchronous detector 6 are connected to each other is formed. In addition, in the flaw detection step, an alternating current having a predetermined frequency is applied to the detecting coil 2 from the alternating-current power supply 5, and a flaw present in the welded pipe P is detected on the basis of, in the output signal of the detecting coil 2 to which an alternating current has been applied, a signal component obtained by the synchronous detection by the synchronous detector 6 with the frequency of the alternating current.

In the bead scrap detection step, the switches S1 and S2 provided in the switching circuit 8 respectively get into states indicated by solid lines in FIG. 3. That is, a state in which the detecting coil 2 is cut off from the alternating-current power supply 5 and the detecting coil 2 and the voltmeter 4 are connected to each other is formed. In addition, in the bead scrap detection step, the application of the alternating current having a predetermined frequency to the detecting coil 2 from the alternating-current power supply 5 is stopped, and the bead scrap B present in the welded pipe P is detected on the basis of the output signal of the detecting coil 2 to which the application of the alternating current has been stopped. Specifically, similar to the first embodiment, the output voltage of the detecting coil 2 is measured using the voltmeter 4, and the bead scrap B present in the welded pipe P is detected on the basis of this measured output voltage.

According to the detection method according to the third embodiment, in the flaw detection step, an alternating current having a predetermined frequency is applied to the detecting coil 2 (the application is turned on), whereby ordinary eddy-current flaw detection using, in the output signal of the detecting coil 2, the signal component obtained by the synchronous detection with the frequency of the applied alternating current becomes possible. In the bead scrap detection step, the application of the alternating current having a predetermined frequency to the detecting coil 2 is stopped (the application is turned off), whereby, similar to the detection method according to the first embodiment, the detecting coil 2 is simply used only to monitor the induced electromotive force generated by the magnetic flux φb of the bead scrap B, and it is possible to detect the bead scrap B on the basis of the output signal of the detecting coil 2.

In the detection method according to the third embodiment, the switching of the switches S1 and S2 provided in the switching circuit 8, that is, the turning of the application of the alternating current to the detecting coil 2 on and off needs to be cyclically repeated at a predetermined cycle. As long as the set repetition cycle is not too long, it is possible to detect both a flaw and the bead scrap B with no misses. Specifically, for example, in a case where the alternating-current frequency is 20 kHz, the turning of the application of the alternating current on and off needs to be cyclically repeated at intervals of approximately three cycles (=0.15 ms) of 20 kHz.

In all of the detection methods according to the first to third embodiments described above, a case where one detecting coil 2 is disposed has been described as an example; however, in a case where only one detecting coil 2 is disposed, there is a concern that the ratio (S/N ratio) of a signal component generated due to the bead scrap B to, in the output signal of the detecting coil 2, a noise signal component generated due to deviation between the central axis of the welded pipe P and the central axis of the detecting coil 2 caused by the vibration of the welded pipe P may be small and it may not be possible to precisely detect the bead scrap B.

In order to precisely detect the bead scrap B, it is preferable to dispose a plurality of detecting coils 2 in the longitudinal direction of the welded pipe P and carry out predetermined signal processing on the output signals of the respective detecting coils 2. Hereinafter, a preferred method will be described using the case of applying the method to the detection method according to the first embodiment as an example.

FIG. 4 is a view for describing a first modification example of the detection method according to the first embodiment.

As shown in FIG. 4, the first modification example of the detection method according to the first embodiment is executed using a detection device 100D. The detection device 100D includes the exciting coil 1, a plurality (three in the example shown in FIG. 4) of detecting coils 2a, 2b, and 2c, a plurality (the same number as the detecting coils, three in the example shown in FIG. 4) of voltmeters 4a, 4b, and 4c as detector, and a signal processor 9. The output voltages measured using the voltmeters 4a to 4c (the output signals of the detecting coils 2a to 2c) are input to the signal processor 9, and signal processing (first to fourth steps described below) is carried out by the signal processor 9. In addition, the detection device 100D includes the direct-current power supply 3 and a laser Doppler speedometer 10.

In the first modification example of the detection method according to the first embodiment, the following first to fourth steps are executed in a second step.

[First Step]

In the first step, the signal processor 9 averages output signals of the detecting coils 2a to 2c output at the same time (output voltages measured by the voltmeters 4a to 4c), thereby computing a first signal. The detector has a first signal computation unit configured to average the output signals of the plurality of detecting coils output at the same time, thereby computing the first signal.

FIG. 5 is a view for schematically describing the content of the first step. FIG. 5(a) shows an output signal of the detecting coil 2a, FIG. 5(b) shows an output signal of the detecting coil 2b, FIG. 5(c) shows an output signal of the detecting coil 2c, and FIG. 5(d) shows an averaged signal. The horizontal axes for the respective signals shown in FIG. 5 indicate distances. This is also true for individual signals shown in FIG. 6 to FIG. 8 described below. For example, the relative movement speed of the welded pipe P detected by the laser Doppler speedometer 10 is input to the signal processor 9, and the signal processor 9 multiplies the input relative movement speed and the time to compute the distance. It is also possible to indicate not the distance, but the time along the horizontal axes of the respective signals.

As shown in FIGS. 5(a) to 5(c), the noise signal components generated by the generation of deviation between the central axis of the welded pipe P and the central axes of the detecting coils 2a to 2c are generated at the same time in all of the detecting coils 2a to 2c. In contrast, signal components generated when the front end (an end on the downstream side in the relative movement direction of the welded pipe P) of the bead scrap B is inserted into the detecting coils 2a to 2c (hereinafter, appropriately referred to as the "bead scrap front end signal components") are generated earliest in the detecting coil 2a located most upstream in the relative movement direction of the welded pipe P, then, generated in the detecting coil 2b, and generated last in the detecting coil 2c located most downstream.

If the voltages of the noise signal components are equal, and the voltages of the bead scrap front end signal components are also equal (voltage V) in all of the detecting coils 2a to 2c, a result as shown in FIG. 5(d) is obtained. That is, in the first signal computed by averaging the output signals of the detecting coils 2a to 2c output at the same time, the voltage of the noise signal component does not change, and the voltage of the bead scrap front end signal component becomes ⅓V.

[Second Step]

In the second step, the signal processor 9 subtracts the first signal computed in the first step from the output signals of the detecting coils 2a to 2c output at the same time, thereby computing second signals corresponding to the detecting coils 2a to 2c. The detector has a second signal computation unit configured to subtract the first signal from the output signals of the plurality of detecting coils output at the same time, thereby computing second signals corresponding to the plurality of detecting coils.

FIG. 6 is a view for schematically describing the content of the second step. FIG. 6(a) shows a process of computing the second signal of the detecting coil 2a, FIG. 6(b) shows a process of computing the second signal of the detecting coil 2b, and FIG. 6(c) shows a process of computing the second signal of the detecting coil 2c.

As shown in FIGS. 6(a) to 6(c), for the second signals of all of the detecting coils 2a to 2c as well, the voltage of the noise signal component ideally becomes zero, and the voltage of the bead scrap front end signal component (the component on the positive side) becomes ⅔V.

[Third Step]

In the third step, the signal processor 9 shifts the horizontal axes of the second signals of the detecting coils 2a to 2c by the separation distance between the detecting coils 2a to 2c and adds the shifted second signals of the detecting coils 2a to 2c computed in the second step to each other, thereby computing a third signal. The detector has a third signal computation unit configured to shift the horizontal axes of the plurality of second signals by the separation distance between the plurality of detecting coils and add the plurality of shifted second signal to each other, thereby computing the third signal.

FIG. 7 is a view for schematically describing the content of the third step. FIG. 7(a) shows the second signal of the detecting coil 2a, FIG. 7(b) shows the second signal of the detecting coil 2b in a shifted state, FIG. 7(c) shows the second signal of the detecting coil 2c in a shifted state, and FIG. 7(d) shows the third signal.

The separation distances (refer to FIG. 4) between the detecting coils 2a to 2c are known in advance and input to the signal processor 9 in advance. For example, the location (location in the longitudinal direction of the welded pipe P) of the detecting coil 2a is regarded as a criterion, a separation distance $\Delta ab$ of the detecting coil 2b relative to the detecting coil 2a and a separation distance $\Delta ac$ of the detecting coil 2c relative to the detecting coil 2a are input to the signal processor 9 in advance. In addition, for example, in a case where the horizontal axes of the second signals of the respective detecting coils 2a to 2c indicate distances, the second signal of the detecting coil 2a is regarded as a criterion, and the horizontal axes of the second signal of the detecting coil 2b and the second signal of the detecting coil 2c are shifted, the bead scrap front end signal component (the component on the positive side) in the second signal of the detecting coil 2b is generated at a location shifted (delayed) relative to the bead scrap front end signal component (the component on the positive side) in the second signal of the detecting coil 2a by the separation distance $\Delta ab$ and is thus shifted (advanced) from a location indicated by a dotted line to a location indicated by a solid line as shown in FIG. 7(b). Similarly, the bead scrap front end signal component (the component on the positive side) in the second signal of the detecting coil 2c is generated at a location shifted (delayed) relative to the bead scrap front end signal component (the component on the positive side) in the second signal of the detecting coil 2a by the separation distance $\Delta ac$ and is thus shifted (advanced) from a location indicated by a broken line to a location indicated by a solid line as shown in FIG. 7(c).

In a case where the horizontal axes of the second signals of the respective detecting coils 2a to 2c indicate times, it is possible to compute distances by multiplying the relative movement speeds of the welded pipe P, which are detected by the laser Doppler speedometer 10 and input to the signal processor 9, and the times and then subtract the distances in the same manner as described above.

The locations in the horizontal axes of the bead scrap front end signal components (the components on the positive side) in the second signals of the detecting coils 2a to 2c shifted as described above coincide with each other, and thus, as shown in FIG. 7(d), in a third signal computed by adding the bead scrap front end signal components to each other, the voltage of the bead scrap front end signal component (the components on the positive side) becomes 2 V.

In the above description, a case where there are three detecting coils 2 has been described as an example; however, generally, as the number of the detecting coils 2 is N (N≥2), the voltage of the bead scrap front end signal component in the first signal shown in FIG. 5(d) becomes (1/N)N. In this case, the voltages of the bead scrap front end signal components (the components on the positive side) in the second signals shown in FIGS. 6(a) to 6(c) become (1−1/N)V. In addition, the voltage of the bead scrap front end signal component (the component on the positive side) in the third signal shown in FIG. 7(d) becomes N(1−1/N)V=(N−1)V. Therefore, the voltage becomes (N−1) times the voltage V of the bead scrap front end signal component in the original output signal of the detecting coil 2 (refer to FIG. 5(a)). In order to set the voltage of the bead scrap front end signal component (the component on the positive side) in the third signal to be larger than the voltage of the bead scrap front end signal component in the original output signal, it is preferable to set N≥3.

[Fourth Step]

In the fourth step, the signal processor 9 detects the bead scrap B present in the welded pipe P on the basis of the third signal computed in the third step. The detector has a first detection unit configured to detect the bead scrap B present in the welded pipe P on the basis of the third signal. In the third signal, the voltage of the noise signal component ideally becomes zero, and the voltage of the bead scrap front end signal component (the component on the positive side) becomes (N−1) times the original voltage, and thus the S/N ratio increases, and it is possible to precisely detect the bead scrap B.

In the first modification example of the detection method according to the first embodiment described above, all of the first to fourth steps are executed in this order, but the third step may be omitted in the modification example.

That is, in a second modification example of the detection method according to the first embodiment, individual steps (1) to (3) described below are executed in the second step.

(1) A step in which the signal processor 9 averages the output signals of the detecting coils 2a to 2c output at the same time, thereby computing the first signal (the same step as the first step).

(2) A step in which the signal processor 9 subtracts the first signal from the output signals of the detecting coils 2a to 2c output at the same time, thereby computing the second signals corresponding to the detecting coils 2a to 2c (the same step as the second step).

(3) A step in which the signal processor 9 detects the bead scrap B present in the welded pipe P on the basis of at least any one of the plurality of second signals (a step relating to the fourth step).

The detector has a second detection unit configured to detect the bead scrap B present in the welded pipe P on the basis of at least any one of the plurality of second signals.

According to the second modification example of the detection method according to the first embodiment, the bead scrap B is detected on the basis of at least any one of the second signals of the detecting coils 2a to 2c shown in FIGS. 6(a) to 6(c). As described above, for the second signal of any of the detecting coils 2a to 2c, the voltage of the noise signal component ideally becomes zero, but the voltage of the bead scrap front end signal component (the component on the positive side) simply decreases to ⅔V, and thus the S/N ratio increases, and it is possible to precisely detect the bead scrap B.

In addition, in the first modification example of the detection method according to the first embodiment described above, all of the first to fourth steps are executed in this order, but the step relating to the fourth step may be executed after the step relating to the third step is first executed in the modification example.

That is, in a third modification example of the detection method according to the first embodiment, individual steps (4) and (5) described below are executed in the second step.

(4) A step in which the signal processor 9 shifts the horizontal axes of the output signals of the detecting coils 2a to 2c by the separation distance between the detecting coils 2a to 2c and adds the shifted output signals of the detecting coils 2a to 2c to each other, thereby computing a fourth signal (a step relating to the third step).

(5) A step in which the signal processor 9 detects the bead scrap B present in the welded pipe P on the basis of the fourth signal (a step relating to the fourth step).

The detector has a fourth signal computation unit configured to shift the horizontal axes of the output signals of the plurality of detecting coils corresponding to the separation distances of the plurality of detecting coils and add the plurality of shifted output signals to each other, thereby computing the fourth signal and a third detection unit configured to detect the bead scrap B present in the welded pipe P on the basis of the fourth signal.

According to the third modification example of the detection method according to the first embodiment, the bead scrap B is detected on the basis of the fourth signal shown in FIG. 8. As shown in FIG. 8, in the fourth signal, the voltage of the noise signal component does not change, and the voltage of the bead scrap front end signal component becomes 3V. Therefore, the S/N ratio increases, and it is possible to precisely detect the bead scrap B.

In the above description, cases where the preferred methods in which the plurality of detecting coils 2 is disposed in the longitudinal direction of the welded pipe P and predetermined signal processing is carried out on the output signals of the respective detecting coils 2 (the first to third modification examples) are applied to the detection method according to the first embodiment have been described as examples, but the present invention is not limited thereto, and it is also possible to apply the preferred methods to the detection methods according to the second embodiment and the third embodiment.

In the case of applying the preferred methods to the detection method according to the second embodiment, it is necessary to dispose the voltmeters 4 and the low pass filters 7 shown in FIG. 2 as many as the detecting coils 2, input the measured voltages measured by the respective voltmeters 4 to the signal processor 9, and execute the first to fourth steps in the case of the first modification example, the steps (1) to (3) in the case of the second modification example, and the steps (4) and (5) in the case of the third modification example.

In addition, in the case of applying the preferred methods to the detection method according to the third embodiment, it is necessary to dispose the voltmeters 4 shown in FIG. 3 as many as the detecting coils 2, input the measured voltages measured by the respective voltmeters 4 to the signal processor 9, and execute the first to fourth steps in the case of the first modification example, the steps (1) to (3) in the case of the second modification example, and the steps (4) and (5) in the case of the third modification example.

In the detection methods according to the first to third embodiments and the first to third modification examples described above, as the exciting coil 1, a penetration-type exciting coil into which a metal pipe P is inserted is used. In the pure penetration-type exciting coil 1, the magnetic paths of magnetic fluxes generated are an open magnetic circuit, and thus the magnetization state of the metal pipe P varies depending on the location of the longitudinal-direction end portion of the metal pipe P. That is, in order to obtain a certain magnetization state, the longitudinal-direction end portion of the metal pipe P needs to be sufficiently apart from the end portion of the exciting coil 1. In other words, there is a concern that, in the longitudinal-direction end portion of the metal pipe P, a region in which the bead scrap B cannot be highly sensitively detected (dead zone) may be present. In order to highly sensitively detect the bead scrap B throughout the entire metal pipe P in the longitudinal direction, it is desirable to reduce this dead zone as much as possible. In order for that, in all cases of the detection methods according to the first to third embodiments and the first to third modification examples, a predetermined yoke member configured to surround the exciting coil 1 and the detecting coil 2 is preferably provided. Hereinafter, this modification example (fourth modification example) will be specifically described.

FIG. 9A and FIG. 9B are views showing the schematic configuration of a detection device 100E used to execute a detection method of the fourth modification example. FIG. 9A is a view showing the schematic configuration of the exciting coil 1, the detecting coil 2, a bobbin 50, and a yoke member 30 provided in the detection device and a cross-sectional view in the case of being seen on a longitudinal section including the central axis line of the welded pipe P. FIG. 9B is a perspective view of FIG. 9A. The left view of FIG. 9B shows a state in which one member piece configuring the yoke member 30 is removed, and the right view shows a state in which the member piece is not removed.

As shown in FIG. 9A, the detection device 100E according to the fourth modification example includes, in addition to the exciting coil 1, the detecting coil 2, and the bobbin 50, the yoke member 30. Although not shown in FIG. 9A and FIG. 9B, the detection device 100E includes a different configurational element depending on which of the first to third embodiments and the first to third modification examples the yoke member 30 of the fourth modification example is applied. For example, in the case of applying the yoke member to the first embodiment, the detection device 100E includes, as configurational elements, the direct-current power supply 3 and the voltmeter 4 in addition to the exciting coil 1, the detecting coil 2, the yoke member 30, and the bobbin 50.

The exciting coil 1 is wound around the outer surface of the hollow bobbin 50 through which the welded pipe P passes. A direct current is applied to the exciting coil 1 from the direct-current power supply 3, the welded pipe P is magnetized in the X direction using the direct current, and magnetic fluxes $\phi$ are generated. In FIG. 9A and FIG. 9B, the magnetic fluxes $\phi$ are shown by broken lines. In addition, the magnetic fluxes $\phi$ shown in the left view of FIG. 9B are magnetic fluxes generated inside the exciting coil 1.

The detecting coil 2 is also, similar to the exciting coil 1, wound around the outer surface of the bobbin 50. However, the detecting coil 2 is wound inside the exciting coil 1 at the X-direction center location of the outer surface of the bobbin 50.

The yoke member 30 has a first opening part 31 which is located upstream (one end side) along the relative movement direction (X direction) of the welded pipe P and into which the welded pipe P is inserted and a second opening part 32 which is located downstream (the other end side) along the relative movement direction of the welded pipe P and into which the welded pipe P is inserted. The first opening part 31 and the second opening part 32 shown in FIG. 9A have a substantially circular shape when seen in the X direction. The yoke member 30 has an outer shape substantially axisymmetric with respect to an axis passing through the first opening part 31 and the second opening part 32 (the central axis in the X direction). The exciting coil 1 and the detecting coil 2 are surrounded by the yoke member 30, the first opening part 31, and the second opening part 32.

The yoke member 30 shown in FIG. 9A and FIG. 9B has a spherical outer shape and is made up of a member piece 30a and a member piece 30b each having a hemispherical outer shape. Specifically, portions (substantially hemispherical portions when seen in the X direction) 31a and 32a each forming the first opening part 31 and the second opening part 32 in the member piece 30a and portions (substantially hemispherical portions when seen in the X direction) 31b and 32b each forming the first opening part 31 and the second opening part 32 in the member piece 30b are each fitted into a groove of a flange portion 51 formed at the end portion of the bobbin 50. Therefore, the respective member pieces 30a and 30b are integrated together and form the yoke member 30 having a spherical outer shape. The end portions of the respective member pieces 30a and 30b on the upstream side in the relative movement direction (X direction) of the welded pipe P, that is, the portions 31a and 31b forming the first opening part 31 in the respective member pieces 30a and 30b are located upstream of the end portions of the exciting coil 1 and the detecting coil 2 on the upstream side in the relative movement direction (X direction) of the welded pipe P. In addition, the end portions of the respective member pieces 30a and 30b on the downstream side in the relative movement direction (X direction) of the welded pipe P, that is, the portions 32a and 32b forming the second opening part 32 in the respective member pieces 30a and 30b are located downstream of the end portions of the exciting coil 1 and the detecting coil 2 on the downstream side in the relative movement direction (X direction) of the welded pipe P. Furthermore, the first opening part 31 and the second opening part 32 are closer to the welded pipe P than the vicinity of the center of the yoke member 30. Therefore, the exciting coil 1 and the detecting coil 2 are surrounded by the yoke member 30, the first opening part 31, and the second opening part 32.

The outer shape of the yoke member 30 shown in FIG. 9A and FIG. 9B is a spherical shape, but is not limited thereto, and it is possible to employ a variety of configurations as long as the yoke member has a substantially axisymmetric outer shape, for example, a spheroid or a column. In addition, the yoke member 30 shown in FIG. 9A and FIG. 9B does not have any openings other than the first opening part 31 and the second opening part 32. However, a magnetic flux generated in the bead scrap B is great, and thus, in a case where the yoke member 30 does not need to be strictly axisymmetric, it is possible to form a slit portion extending along the central axis in, for example, a part of the yoke member 30 in the circumferential direction (a direction around the central axis) and to reduce the weight of the yoke member 30.

As described above, the detection device 100E according to the fourth modification example includes the yoke member 30 having a substantially axisymmetric outer shape, which surrounds the exciting coil 1 and the detecting coil 2, and thus it is possible to forcibly introduce magnetic paths (refer to FIG. 9A and FIG. 9B) of the magnetic fluxes $\phi$ generated in the welded pipe P by the magnetization of the exciting coil 1 into the yoke member 30 even in any portion of the welded pipe P in the circumferential direction. That is, the magnetic paths of the magnetic fluxes $\phi$ generated in the welded pipe P becomes a closed magnetic circuit, and thus, unlike the case of an open magnetic circuit, the magnetization state of the welded pipe P is not easily affected by the location of the end portion of the welded pipe P, and it is possible to reduce the dead zone in the pipe end portion. In addition, the magnetic fluxes $\phi$ generated in the welded pipe P become substantially uniform in any portions of the welded pipe P in the circumferential direction, and, regardless of the portion of the welded pipe P in the circumferential direction in which the bead scrap B is present, it is possible to highly sensitively detect the bead scrap B.

EXAMPLES

Hereinafter, an example of detecting a bead scrap B using the detection method according to the fourth modification example shown in FIG. 9A and FIG. 9B will be described.

A yoke member 30 in which the thickness of the yoke member 30 was 30 mm was manufactured in a structure obtained by hollowing a sphere-equivalent portion having a diameter of 100 mm from an iron ball having a diameter of 160 mm. The yoke member 30 was provided with a first opening part 31 located on the upstream side in the relative movement direction (X direction) of a welded pipe P and a second opening part 32 located on the downstream side in the relative movement direction of the welded pipe P were provided. The diameters of the first opening part 31 and the second opening part 32 were both 55 mm. Rollers (not shown) for suppressing a pass line of the welded pipe P were disposed on the upstream side in the relative movement direction (X direction) of the first opening part 31 and the downstream side in the relative movement direction (X direction) of the second opening part 32 of the yoke member 30. These rollers suppress a pass line fluctuation in vertical and horizontal directions occurring during the relative movement (relative movement relative to exciting coils 1 and a detecting coil 2) of the welded pipe P within a radial range of 1 mm from the central axis of the welded pipe P. The welded pipe P having a length of 1 m, an outer diameter of 35 mm, and a thickness of 3 mm was inserted into this yoke member 30. The welded pipe P was disposed such that a position 200 mm apart from the front end (an end on the downstream side in the relative movement direction) of the welded pipe P was located at the center of the yoke member 30 in the X-axis direction. The bead scrap B having a 1 mm×2 mm cross section and a length of 900 mm was inserted into the inside of the welded pipe P. The bead scrap was fixed such that the rear end (an end on the upstream side in the relative movement direction) of the bead scrap B was located 100 mm apart from the rear end (an end on the upstream side in the relative movement direction) of the welded pipe P. The number of turns (the total of the numbers of turns) of the exciting coils 1 was set to 200, and the number of turns of the detecting coil 2 was set to 20. A direct current of 10 A was caused to flow from a direct-current power supply 3 to the exciting coils 1, thereby magnetizing the welded pipe P and the bead scrap B using the direct current. In this state, the welded pipe P was moved in the longitudinal direction at a speed of 1 m/sec.

FIG. 10 is a graph showing an example of the output signal of the detecting coil 2 obtained using the detection method according to the fourth modification example under the above-described conditions. Specifically, FIG. 10 is an example of the output signal of the detecting coil 2 obtained when the rear end of the bead scrap B passes through the detecting coil 2. The vertical axis in FIG. 10 indicates the output voltage of the detecting coil 2, and the horizontal axis indicates sampling numbers when the output signal waveform is sampled at predetermined sampling pitches.

As shown in FIG. 10, the output voltage of the detecting coil 2 significantly decreased when the rear end of the bead scrap B passes through the detecting coil 2. Therefore, in a case where the output voltage of the detecting coil 2 is compared with, for example, a predetermined negative threshold value and exceeds the threshold value (smaller than the threshold value), it is possible to determine that the bead scrap B is present in the welded pipe P (a place at which the output voltage exceeds the threshold value is determined as the rear end of the bead scrap B).

INDUSTRIAL APPLICABILITY

According to the present invention, it is possible to highly sensitively detect a metal residue such as a bead scrap present in an electric-resistance-welded steel pipe such as an electric-resistance-welded pipe. Therefore, the present invention is highly industrially applicable.

BRIEF DESCRIPTION OF THE REFERENCE SYMBOLS

1 Exciting coil
2, 2a, 2b, 2c Detecting coil
3 Direct-current power supply
4, 4a, 4b, 4c Voltmeter
5 Alternating-current power supply
6 Synchronous detector
7 Low pass filter
8 Switching circuit
9 Signal processor
30 Yoke member
100, 100A, 100B, 100C, 100D, 100E Detection device
P Metal pipe (welded pipe)
B Metal residue (bead scrap)

The invention claimed is:
1. A method for detecting a metal residue present in an electric-resistance-welded steel pipe, the method comprising:
a first step of inserting the electric-resistance-welded steel pipe into an exciting coil while relatively moving the electric-resistance-welded steel pipe in a longitudinal direction and magnetizing the electric-resistance-welded steel pipe using a direct current at a field intensity capable of magnetizing the electric-resistance-welded steel pipe and the metal residue up to a magnetic saturation state by the exciting coil; and
a second step of inserting the electric-resistance-welded steel pipe into a detecting coil while relatively moving the electric-resistance-welded steel pipe in the longitudinal direction, detecting an induced electromotive force generated in the detecting coil by a change in a magnetic flux caused by the direct-current magnetization by the exciting coil in the first step as an output signal of the detecting coil, and detecting the metal residue present in the electric-resistance-welded steel pipe on the basis of the output signal of the detecting coil.
2. The method for detecting a metal residue present in an electric-resistance-welded steel pipe according to claim 1, wherein, in the second step, an alternating current is not applied to the detecting coil.
3. The method for detecting a metal residue present in an electric-resistance-welded steel pipe according to claim 2, wherein the metal residue present in the electric-resistance-welded steel pipe is detected by a yoke member having a first opening part which is located on one end side along the longitudinal direction of the electric-resistance-welded steel pipe and into which the electric-resistance-welded steel pipe is inserted and a second opening part which is located on the other end side along the longitudinal direction of the electric-resistance-welded steel pipe and into which the electric-resistance-welded steel pipe is inserted, having an outer shape substantially axisymmetric with respect to an axis passing through the first opening part and the second opening part, and surrounding the exciting coil and the detecting coil.

4. The method for detecting a metal residue present in an electric-resistance-welded steel pipe according to claim 1,
wherein the second step includes
an alternating-current application step of applying an alternating current having a predetermined frequency to the detecting coil,
a flaw detection step of detecting a flaw present in the electric-resistance-welded steel pipe on the basis of a signal component obtained by synchronous detection with the frequency of the alternating current, in the output signal of the detecting coil to which the alternating current is applied, and
a metal residue detection step of detecting the metal residue present in the electric-resistance-welded steel pipe on the basis of a signal component permeating a low pass filter having the frequency of the alternating current as a cutoff frequency, in the output signal of the detecting coil to which the alternating current is applied.

5. The method for detecting a metal residue present in an electric-resistance-welded steel pipe according to claim 4,
wherein the metal residue present in the electric-resistance-welded steel pipe is detected by a yoke member having a first opening part which is located on one end side along the longitudinal direction of the electric-resistance-welded steel pipe and into which the electric-resistance-welded steel pipe is inserted and a second opening part which is located on the other end side along the longitudinal direction of the electric-resistance-welded steel pipe and into which the electric-resistance-welded steel pipe is inserted, having an outer shape substantially axisymmetric with respect to an axis passing through the first opening part and the second opening part, and surrounding the exciting coil and the detecting coil.

6. The method for detecting a metal residue present in an electric-resistance-welded steel pipe according to claim 1,
wherein the second step includes
a flaw detection step of applying an alternating current having a predetermined frequency to the detecting coil and detecting a flaw present in the electric-resistance-welded steel pipe on the basis of a signal component obtained by synchronous detection with the frequency of the alternating current, in the output signal of the detecting coil to which the alternating current is applied, and
a metal residue detection step of stopping application of the alternating current having a predetermined frequency to the detecting coil and detecting the metal residue present in the electric-resistance-welded steel pipe on the basis of the output signal of the detecting coil to which the application of the alternating current is stopped.

7. The method for detecting a metal residue present in an electric-resistance-welded steel pipe according to claim 6,
wherein the metal residue present in the electric-resistance-welded steel pipe is detected by a yoke member having a first opening part which is located on one end side along the longitudinal direction of the electric-resistance-welded steel pipe and into which the electric-resistance-welded steel pipe is inserted and a second opening part which is located on the other end side along the longitudinal direction of the electric-resistance-welded steel pipe and into which the electric-resistance-welded steel pipe is inserted, having an outer shape substantially axisymmetric with respect to an axis passing through the first opening part and the second opening part, and surrounding the exciting coil and the detecting coil.

8. The method for detecting a metal residue present in an electric-resistance-welded steel pipe according to claim 1,
wherein a plurality of the detecting coils is disposed in the longitudinal direction of the electric-resistance-welded steel pipe, and
the second step includes
a step of averaging the output signals of the plurality of detecting coils output at the same time to compute a first signal,
a step of subtracting the first signal from the output signals of the plurality of detecting coils output at the same time to compute second signals respectively corresponding to the plurality of detecting coils,
a step of shifting horizontal axes of the plurality of second signals by a separation distance between the plurality of detecting coils and adding the plurality of shifted second signals to each other to compute a third signal, and
a step of detecting the metal residue present in the electric-resistance-welded steel pipe on the basis of the third signal.

9. The method for detecting a metal residue present in an electric-resistance-welded steel pipe according to claim 8,
wherein the metal residue present in the electric-resistance-welded steel pipe is detected by a yoke member having a first opening part which is located on one end side along the longitudinal direction of the electric-resistance-welded steel pipe and into which the electric-resistance-welded steel pipe is inserted and a second opening part which is located on the other end side along the longitudinal direction of the electric-resistance-welded steel pipe and into which the electric-resistance-welded steel pipe is inserted, having an outer shape substantially axisymmetric with respect to an axis passing through the first opening part and the second opening part, and surrounding the exciting coil and the detecting coil.

10. The method for detecting a metal residue present in an electric-resistance-welded steel pipe according to claim 1,
wherein a plurality of the detecting coils is disposed in the longitudinal direction of the electric-resistance-welded steel pipe, and
the second step includes
a step of averaging the output signals of the plurality of detecting coils output at the same time to compute a first signal,
a step of subtracting the first signal from the output signals of the plurality of detecting coils output at the same time to compute second signals respectively corresponding to the plurality of detecting coils, and
a step of detecting the metal residue present in the electric-resistance-welded steel pipe on the basis of at least any one of the plurality of second signals.

11. The method for detecting a metal residue present in an electric-resistance-welded steel pipe according to claim 10,
wherein the metal residue present in the electric-resistance-welded steel pipe is detected by a yoke member having a first opening part which is located on one end side along the longitudinal direction of the electric-resistance-welded steel pipe and into which the electric-resistance-welded steel pipe is inserted and a second opening part which is located on the other end side along the longitudinal direction of the electric-resistance-welded steel pipe and into which the electricresistance-welded steel pipe is inserted, having an outer shape substantially axisymmetric with respect to an axis passing through the first opening part and the second opening part, and surrounding the exciting coil and the detecting coil.

12. The method for detecting a metal residue present in an electric-resistance-welded steel pipe according to claim 1, wherein a plurality of the detecting coils is disposed in the longitudinal direction of the electric-resistance-welded steel pipe, and
the second step includes
a step of shifting horizontal axes of the output signals of the plurality of detecting coils by a separation distance between the plurality of detecting coils and adding the plurality of shifted output signals to each other to compute a fourth signal, and
a step of detecting the metal residue present in the electric-resistance-welded steel pipe on the basis of the fourth signal.

13. The method for detecting a metal residue present in an electric-resistance-welded steel pipe according to claim 12, wherein the metal residue present in the electric-resistance-welded steel pipe is detected by a yoke member having a first opening part which is located on one end side along the longitudinal direction of the electric-resistance-welded steel pipe and into which the electric-resistance-welded steel pipe is inserted and a second opening part which is located on the other end side along the longitudinal direction of the electric-resistance-welded steel pipe and into which the electric-resistance-welded steel pipe is inserted, having an outer shape substantially axisymmetric with respect to an axis passing through the first opening part and the second opening part, and surrounding the exciting coil and the detecting coil.

14. The method for detecting a metal residue present in an electric-resistance-welded steel pipe according to claim 1, wherein the metal residue present in the electric-resistance-welded steel pipe is detected by a yoke member having a first opening part which is located on one end side along the longitudinal direction of the electric-resistance-welded steel pipe and into which the electric-resistance-welded steel pipe is inserted and a second opening part which is located on the other end side along the longitudinal direction of the electric-resistance-welded steel pipe and into which the electric-resistance-welded steel pipe is inserted, having an outer shape substantially axisymmetric with respect to an axis passing through the first opening part and the second opening part, and surrounding the exciting coil and the detecting coil.

15. A device for detecting a metal residue present in an electric-resistance-welded steel pipe, the device comprising:
an exciting coil into which the electric-resistance-welded steel pipe relatively moving in a longitudinal direction is inserted and which magnetizes the electric-resistance-welded steel pipe using a direct current at a field intensity capable of magnetizing the electric-resistance-welded steel pipe and the metal residue up to a magnetic saturation state;
a detecting coil into which the electric-resistance-welded steel pipe relatively moving in the longitudinal direction is inserted and which detects and outputs an induced electromotive force generated by a change in a magnetic flux caused by direct-current magnetization by the exciting coil; and
a detector for detecting the metal residue present in the electric-resistance-welded steel pipe on the basis of an output signal of the detecting coil.

16. The device for detecting a metal residue present in an electric-resistance-welded steel pipe according to claim 15, wherein a plurality of the detecting coils is disposed in the longitudinal direction of the electric-resistance-welded steel pipe, and
the detector includes
a first signal computation unit configured to average the output signals of the plurality of detecting coils output at the same time to compute a first signal,
a second signal computation unit configured to subtract the first signal from the output signals of the plurality of detecting coils output at the same time to compute second signals respectively corresponding to the plurality of detecting coils,
a third signal computation unit configured to shift horizontal axes of the plurality of second signals by a separation distance between the plurality of detecting coils and adding the plurality of shifted second signals to each other to compute a third signal, and
a first detection unit configured to detect the metal residue present in the electric-resistance-welded steel pipe on the basis of the third signal.

17. The device for detecting a metal residue present in an electric-resistance-welded steel pipe according to claim 16, the device further comprising:
a yoke member having a first opening part which is located on one end side along the longitudinal direction of the electric-resistance-welded steel pipe and into which the electric-resistance-welded steel pipe is inserted and a second opening part which is located on the other end side along the longitudinal direction of the electric-resistance-welded steel pipe and into which the electric-resistance-welded steel pipe is inserted, having an outer shape substantially axisymmetric with respect to an axis passing through the first opening part and the second opening part, and surrounding the exciting coil and the detecting coil.

18. The device for detecting a metal residue present in an electric-resistance-welded steel pipe according to claim 15, wherein a plurality of the detecting coils is disposed in the longitudinal direction of the electric-resistance-welded steel pipe, and
the detector includes
a first signal computation unit configured to average the output signals of the plurality of detecting coils output at the same time to compute a first signal,
a second signal computation unit configured to subtract the first signal from the output signals of the plurality of detecting coils output at the same time to compute second signals respectively corresponding to the plurality of detecting coils, and
a second detection unit configured to detect the metal residue present in the electric-resistance-welded steel pipe on the basis of at least any one of the plurality of second signals.

19. The device for detecting a metal residue present in an electric-resistance-welded steel pipe according to claim 18, the device further comprising:
a yoke member having a first opening part which is located on one end side along the longitudinal direction of the electric-resistance-welded steel pipe and into which the electric-resistance-welded steel pipe is inserted and a second opening part which is located on the other end side along the longitudinal direction of the electric-resistance-welded steel pipe and into which the electric-resistance-welded steel pipe is inserted, having an outer shape substantially axisymmetric with respect to an axis passing through the first opening part and the second opening part, and surrounding the exciting coil and the detecting coil.

20. The device for detecting a metal residue present in an electric-resistance-welded steel pipe according to claim 15,
wherein a plurality of the detecting coils is disposed in the longitudinal direction of the electric-resistance-welded steel pipe, and
the detector includes
a signal computation unit configured to shift horizontal axes of the output signals of the plurality of detecting coils by a separation distance between the plurality of detecting coils and adding the plurality of shifted output signals to each other to compute a fourth signal, and
a third detection unit configured to detect the metal residue present in the electric-resistance-welded steel pipe on the basis of the fourth signal.

21. The device for detecting a metal residue present in an electric-resistance-welded steel pipe according to claim 20, the device further comprising:
a yoke member having a first opening part which is located on one end side along the longitudinal direction of the electric-resistance-welded steel pipe and into which the electric-resistance-welded steel pipe is inserted and a second opening part which is located on the other end side along the longitudinal direction of the electric-resistance-welded steel pipe and into which the electric-resistance-welded steel pipe is inserted, having an outer shape substantially axisymmetric with respect to an axis passing through the first opening part and the second opening part, and surrounding the exciting coil and the detecting coil.

22. The device for detecting a metal residue present in an electric-resistance-welded steel pipe according to claim 15, the device further comprising:
a yoke member having a first opening part which is located on one end side along the longitudinal direction of the electric-resistance-welded steel pipe and into which the electric-resistance-welded steel pipe is inserted and a second opening part which is located on the other end side along the longitudinal direction of the electric-resistance-welded steel pipe and into which the electric-resistance-welded steel pipe is inserted, having an outer shape substantially axisymmetric with respect to an axis passing through the first opening part and the second opening part, and surrounding the exciting coil and the detecting coil.

\* \* \* \* \*